(12) United States Patent
Yamasaki et al.

(10) Patent No.: US 8,136,800 B2
(45) Date of Patent: Mar. 20, 2012

(54) DEVICE AND METHOD FOR INCREASING BLOOD FLOW AND INSULIN-LIKE GROWTH FACTOR

(75) Inventors: Kazuyuki Yamasaki, Hiroshima (JP); Takahide Miyamoto, Fukuyama (JP); Kazumi Chuhjoh, Takamatsu (JP); Masaki Kataoka, Fukuyama (JP)

(73) Assignee: Sharp Kabushiki Kaisha, Osaka (JP)

( * ) Notice: Subject to any disclaimer, the term of this patent is extended or adjusted under 35 U.S.C. 154(b) by 1034 days.

(21) Appl. No.: 12/035,457

(22) Filed: Feb. 22, 2008

(65) Prior Publication Data
US 2008/0206362 A1 Aug. 28, 2008

(30) Foreign Application Priority Data

Feb. 28, 2007 (JP) ................................. 2007-050639

(51) Int. Cl.
*B01F 3/04* (2006.01)
(52) U.S. Cl. ........................ 261/122.1; 261/124; 261/29
(58) Field of Classification Search ........................ None
See application file for complete search history.

(56) References Cited

U.S. PATENT DOCUMENTS

| | | | | | |
|---|---|---|---|---|---|
| 3,842,446 | A | * | 10/1974 | Hunhausen et al. | 4/541.2 |
| 5,571,516 | A | * | 11/1996 | Tezuka et al. | 424/401 |
| 2004/0238975 | A1 | * | 12/2004 | Sakakibara et al. | 261/100 |
| 2004/0261167 | A1 | * | 12/2004 | Panopoulos | 4/490 |
| 2006/0054205 | A1 | | 3/2006 | Yabe et al. | |
| 2006/0284325 | A1 | * | 12/2006 | Kohama et al. | 261/122.1 |
| 2009/0117241 | A1 | | 5/2009 | Tsuji | |
| 2009/0321331 | A1 | * | 12/2009 | Hassan et al. | 210/150 |

FOREIGN PATENT DOCUMENTS

| | | |
|---|---|---|
| JP | 63-230623 | 9/1988 |
| JP | 10-155858 | 6/1998 |
| JP | 2002-037725 | 2/2002 |
| JP | 2002-053470 | 2/2002 |
| JP | 2002-068959 | 3/2002 |
| JP | 2002-191518 | 7/2002 |
| JP | 2003-334548 | 11/2003 |
| JP | 2004-121962 | 4/2004 |
| JP | 2004-321959 | 11/2004 |
| JP | 2006-239353 | 9/2006 |
| JP | 2006-320675 | 11/2006 |
| JP | 2007-054655 A | 3/2007 |
| JP | 2007-130591 A | 5/2007 |
| JP | 3131357 | 5/2007 |
| JP | 2007-215824 A | 8/2007 |
| JP | 2008-142173 A | 6/2008 |
| KR | 2003-0024455 | 3/2003 |
| WO | 03/027025 | 4/2003 |

OTHER PUBLICATIONS

Kenji Okajima et al.; "Application of micro bubbles to medical treatment and its possibilities"; Clean Technology; vol. 17, No. 1; pp. 17-18; 2007. (Partial translation of relevant portions provided).

M. Ueda et al., "The Effects on Peripheral Circulation of Bathing Using a New $CO_2$ Bath-Water Generator", The Journal of Japanese society of Balneology, Climatology and Physical medicine, Aug. 1995, vol. 58, No. 4, p. 249-256 (partial English translation provided).

H. Yorozu et al., "Research for Carbon Dioxide Bathing II. An increase of Dermal Blood Flow by the $CO_2$ Preparation", The Journal of Japanese society of Balneology, Climatology and Physical medicine, May 1984, vol. 47, No. 3.4, p. 130-136 (partial English translation provided).

S. Watanabe et al., "The Effects of Bathing with Inorganic Salts and Carbon Dioxide on Body Temperature, Systemic Circulation, and Food Ingestion and Absorption", The Journal of Japanese society of Balneology, Climatology and Physical medicine, May 2006, vol. 69, No. 3, p. 167-178 (partial English translation provided).

H. Yorozu et al., "The Effects of Crude Drug Extracts Bathing", The Journal of Japanese society of Balneology, Climatology and Physical medicine, Feb. 1992, vol. 55, No. 2, p. 105-112 (partial English translation provided).

* cited by examiner

*Primary Examiner* — Johann Richter
*Assistant Examiner* — Jessica Kassa
(74) *Attorney, Agent, or Firm* — Renner, Otto, Boisselle & Sklar, LLP

(57) ABSTRACT

In order to provide a device and a method for increasing blood flow and an insulin-like growth factor with use of a large amount of carbonic gas nano bubbles, the device of the present invention includes: a bathtub 1; and a nano bubble-producing section 41 for producing carbonic gas nano bubbles in bath water in the bathtub 1.

12 Claims, 22 Drawing Sheets

FIG. 17 (b)

| 7_01.$ls | | | | | | | |
|---|---|---|---|---|---|---|---|
| channel diameter (lower limit) μm | frequency volume % | channel diameter (lower limit) μm | frequency volume % | channel diameter (lower limit) μm | frequency volume % | channel diameter (lower limit) μm | frequency volume % |
| 0.040 | 0 | 0.721 | 0.096 | 12.99 | 0 | 234.0 | 0 |
| 0.044 | 0 | 0.791 | 0.0075 | 14.26 | 0 | 256.9 | 0 |
| 0.048 | 0 | 0.868 | 0 | 15.65 | 0 | 282.1 | 0 |
| 0.053 | 0 | 0.953 | 0 | 17.18 | 0 | 309.6 | 0 |
| 0.058 | 0 | 1.047 | 0 | 18.86 | 0 | 339.9 | 0 |
| 0.064 | 0 | 1.149 | 0.0024 | 20.71 | 0 | 373.1 | 0 |
| 0.070 | 0 | 1.261 | 0.036 | 22.73 | 0 | 409.6 | 0 |
| 0.077 | 0 | 1.384 | 0.20 | 24.95 | 0 | 449.7 | 0 |
| 0.084 | 0 | 1.520 | 0.53 | 27.39 | 0 | 493.6 | 0 |
| 0.093 | 0 | 1.668 | 0.89 | 30.07 | 0 | 541.9 | 0 |
| 0.102 | 0 | 1.832 | 1.07 | 33.01 | 0 | 594.8 | 0 |
| 0.112 | 0.0016 | 2.011 | 1.03 | 36.24 | 0 | 653.0 | 0 |
| 0.122 | 0.026 | 2.207 | 0.86 | 39.78 | 0 | 716.8 | 0 |
| 0.134 | 0.16 | 2.423 | 0.70 | 43.67 | 0 | 786.9 | 0 |
| 0.148 | 0.51 | 2.660 | 0.62 | 47.94 | 0 | 863.9 | 0 |
| 0.162 | 1.09 | 2.920 | 0.66 | 52.62 | 0 | 948.3 | 0 |
| 0.178 | 1.88 | 3.205 | 0.74 | 57.77 | 0 | 1041 | 0 |
| 0.195 | 2.90 | 3.519 | 0.81 | 63.41 | 0 | 1143 | 0 |
| 0.214 | 4.22 | 3.863 | 0.83 | 69.61 | 0 | 1255 | 0 |
| 0.235 | 5.87 | 4.240 | 0.74 | 76.42 | 0 | 1377 | 0 |
| 0.258 | 7.66 | 4.655 | 0.53 | 83.89 | 0 | 1512 | 0 |
| 0.284 | 9.28 | 5.110 | 0.26 | 92.09 | 0 | 1660 | 0 |
| 0.311 | 10.3 | 5.610 | 0.078 | 101.1 | 0 | 1822 | 0 |
| 0.342 | 10.6 | 6.158 | 0.011 | 111.0 | 0 | 2000 | |
| 0.375 | 10.0 | 6.760 | 0.00048 | 121.8 | 0 | | |
| 0.412 | 8.61 | 7.421 | 0 | 133.7 | 0 | | |
| 0.452 | 6.68 | 8.147 | 0 | 146.8 | 0 | | |
| 0.496 | 4.64 | 8.943 | 0 | 161.2 | 0 | | |
| 0.545 | 2.86 | 9.818 | 0 | 176.9 | 0 | | |
| 0.598 | 1.42 | 10.78 | 0 | 194.2 | 0 | | |
| 0.656 | 0.51 | 11.83 | 0 | 213.2 | 0 | | |

FIG. 17 (c)

| statistic of volume (arithmetic average) 7_01.$ls |
| --- |
| calculation from 0.040 μm to 2000 μm |
| volume 100% |
| average diameter: 0.629 μm    S.D.: 0.876 μm |
| median diameter: 0.361 μm    dispersion: 0.768 μm$^2$ |
| most frequent diameter: 0.358 μm    C.V.: 139% |

FIG. 18 (b)

| 3_01.$ls | | | | | | | |
|---|---|---|---|---|---|---|---|
| channel diameter (lower limit) µm | frequency volume % | channel diameter (lower limit) µm | frequency volume % | channel diameter (lower limit) µm | frequency volume % | channel diameter (lower limit) µm | frequency volume % |
| 0.040 | 0 | 0.721 | 0 | 12.99 | 0 | 234.0 | 0 |
| 0.044 | 0 | 0.791 | 0 | 14.26 | 0 | 256.9 | 0 |
| 0.048 | 0 | 0.868 | 0 | 15.65 | 0 | 282.1 | 0 |
| 0.053 | 0 | 0.953 | 0 | 17.18 | 0 | 309.6 | 0 |
| 0.058 | 0 | 1.047 | 0 | 18.86 | 0 | 339.9 | 0 |
| 0.064 | 0 | 1.149 | 0 | 20.71 | 0 | 373.1 | 0 |
| 0.070 | 0 | 1.261 | 0 | 22.73 | 0 | 409.6 | 0 |
| 0.077 | 0 | 1.384 | 0 | 24.95 | 0 | 449.7 | 0 |
| 0.084 | 0 | 1.520 | 0 | 27.39 | 0 | 493.6 | 0 |
| 0.093 | 0 | 1.668 | 0 | 30.07 | 0 | 541.9 | 0 |
| 0.102 | 0 | 1.832 | 0 | 33.01 | 0 | 594.8 | 0 |
| 0.112 | 0 | 2.011 | 0 | 36.24 | 0 | 653.0 | 0 |
| 0.122 | 0 | 2.207 | 0 | 39.78 | 0 | 716.8 | 0 |
| 0.134 | 0 | 2.423 | 0 | 43.67 | 0 | 786.9 | 0 |
| 0.148 | 0 | 2.660 | 0 | 47.94 | 0 | 863.9 | 0 |
| 0.162 | 0 | 2.920 | 0 | 52.62 | 0 | 948.3 | 0 |
| 0.178 | 0 | 3.205 | 0 | 57.77 | 0 | 1041 | 0 |
| 0.195 | 0 | 3.519 | 0 | 63.41 | 0 | 1143 | 0 |
| 0.214 | 0 | 3.863 | 0 | 69.61 | 0 | 1255 | 0 |
| 0.235 | 0 | 4.240 | 0 | 76.42 | 0 | 1377 | 0 |
| 0.258 | 0 | 4.655 | 0 | 83.89 | 0 | 1512 | 0 |
| 0.284 | 0 | 5.110 | 0 | 92.09 | 0 | 1660 | 0 |
| 0.311 | 0 | 5.610 | 0 | 101.1 | 0 | 1822 | 0 |
| 0.342 | 0 | 6.158 | 0 | 111.0 | 0 | 2000 | |
| 0.375 | 0 | 6.760 | 0 | 121.8 | 0 | | |
| 0.412 | 0 | 7.421 | 0 | 133.7 | 0 | | |
| 0.452 | 0 | 8.147 | 0 | 146.8 | 0 | | |
| 0.496 | 0 | 8.943 | 0 | 161.2 | 0 | | |
| 0.545 | 0 | 9.818 | 0 | 176.9 | 0 | | |
| 0.598 | 0 | 10.78 | 0 | 194.2 | 0 | | |
| 0.656 | 0 | 11.83 | 0 | 213.2 | 0 | | |

FIG. 18 (c)

| statistic of volume (arithmetic average) 3_01.$ls |
| --- |
| calculation from 0.040 μm to 2000 μm |
| volume 0% |
| average diameter: 0.000 μm   S.D.: 0 μm |
| median diameter: 0.000 μm   dispersion: 0 μm$^2$ |
| most frequent diameter: 0.000 μm   C.V.: 0% |

DEVICE AND METHOD FOR INCREASING BLOOD FLOW AND INSULIN-LIKE GROWTH FACTOR

This non-provisional application claims priority under 35 U.S.C. §119(a) on Patent Application No. 2007-050639 filed in Japan on Feb. 28, 2007, the entire contents of which are hereby incorporated by reference.

FIELD OF THE INVENTION

The present invention relates to a device and a method for increasing blood flow and an insulin-like growth factor with use of carbonic bubbles.

BACKGROUND OF THE INVENTION

It is known that bubbles with a small diameter have various physiological functions. Nowadays, much attention is paid to a technique for producing such bubbles and to effects exerted by such bubbles.

Such bubbles are classified into micro bubbles, micro-nano bubbles, and nano bubbles, according to their diameter. Specifically, micro bubbles have a diameter ranging from 10 μm to several ten μm at a time they are produced, micro-nano bubbles have a diameter ranging from several hundred nm to 10 μm at a time they are produced, and nano bubbles have a diameter of not more than several hundred nm at a time they are produced. Micro bubbles may be partially converted into micro-nano bubbles due to contraction after they are produced.

Studies of micro bubbles have advanced greatly, and various physiological functions of micro bubbles have been discovered. For example, Non-Patent Document 1 (Hitoshi Okajima, "Application of micro bubbles to medical treatment and its possibilities", Clean Technology, 2007, Vol. 17, No. 1) describes physiological functions of micro bubbles: (1) function for promoting growth of oysters and scallops; (2) function for promoting production of an insulin-like growth factor-1; and (3) function for increasing blood flow.

Furthermore, Patent Document 1 (Japanese Unexamined Patent Publication No. 2004-321959 (Tokukai 2004-321959; published on Nov. 18, 2004)) describes that a waste-liquid treatment device using micro bubbles made of ozone gas (ozone micro bubbles) has been conventionally used. The waste-liquid treatment device produces micro bubbles made of ozone gas, by mixing ozone gas from an ozone-producing device and a waste liquid with use of a pressure pump. The micro bubbles chemically react with organic matters in the waste liquid, so that the organic matters in the waste liquid are oxidized and decomposed.

Furthermore, Patent Document 2 (Japanese Unexamined Patent Publication No. 2006-320675 (Tokukai 2006-320675; published on Nov. 30, 2006)) describes that a method and a device for producing micro bubbles made of carbon dioxide (carbonic gas micro bubbles) have been conventionally used. Patent Document 2 describes that the micro bubbles made of carbon dioxide can be produced by providing a carbonic gas container and a pressure-reducing valve in an air-introducing system of a micro bubble-producing device and supplying carbonic gas to the air-introducing system with a certain pressure and certain flow volume. Efficiency in solution of carbonic gas is nearly 100% of theoretical efficiency, and therefore only a small amount of carbonic gas is required, which is economic. Furthermore, Patent Document 2 describes that the device is compact.

However, the above micro bubble techniques have a problem that the techniques cannot fully make use of physiological functions of micro bubbles. For example, only a small amount of the carbonic gas micro bubbles is absorbed via skin, resulting in that the function for promoting production of an insulin-like growth factor-1 and the function for increasing blood flow are not fully performed. For that reason, nowadays, much attention is paid to nano bubbles that have further smaller diameter than that of micro bubbles, and to a device and a method for producing the nano bubbles.

For example, Patent Document 3 (Japanese Unexamined Patent Publication No. 2003-334548 (Tokukai 2003-334548; published on Nov. 25, 2003)) describes that a method for producing nano bubbles from a liquid as a raw material has been conventionally used. The method includes a step (1) of, in a liquid, decomposing and gasifying a part of the liquid, a step (2) of, in a liquid, applying supersonic waves to the liquid, or a step (3) of, in a liquid, decomposing and gasifying a part of the liquid and applying supersonic waves to the liquid. It is described that the step of decomposing and gasifying a part of the liquid may be carried out through electrolysis or photolysis.

Furthermore, Patent Document 4 (Japanese Unexamined Patent Publication No. 2004-121962 (Tokukai 2004-121962; published on Apr. 22, 2004)) describes that a method for using nano bubbles and various devices using nano bubbles have been conventionally used. More specifically, Patent Document 4 describes that nano bubbles reduce a buoyant force, increase a surface area, increase surface activity, produce a local high pressure area, or realize electrostatic polarization, thereby performing surface-active function and fungicidal action. Furthermore, Patent Document 4 describes a technique for cleaning various objects and polluted water by using the surface-active function and the fungicidal action of nano bubbles. Furthermore, Patent Document 4 describes a method for curing fatigue of a living body with use of nano bubbles. Furthermore, Patent Document 4 describes production of nano bubbles by electrolyzing water and applying supersonic wave vibration to the water.

However, the conventional devices and methods for producing nano bubbles cannot produce a large amount of carbonic gas nano bubbles and therefore the devices and the methods cannot fully make use of physiological functions of carbonic gas nano bubbles (e.g. function for increasing blood flow and function for promoting production of insulin-like growth factor-1).

It has been widely known that carbonic gas included in a carbonate spring increases blood flow. Hot springs where concentration of carbonic gas in a carbonate spring is approximately 1000 ppm exist in Europe (e.g. Germany), and such hot springs are used for various medical treatments. In contrast, hot springs where concentration of carbonic gas in a carbonate spring is approximately 1000 ppm do not exist in Japan. Therefore, for medical treatment, it is necessary to produce carbonic gas nano bubbles of 1000 ppm or more in carbonic gas concentration. However, the conventional devices and methods for producing nano bubbles cannot produce carbonic gas nano bubbles of 1000 ppm or more in carbonic gas concentration.

It is deemed that carbonic gas nano bubbles exert their effects on a human body greatly at a time when the diameter of each carbonic gas nano bubble is not more than 1 μm and is approximately several ten nm. However, the conventional devices and methods for producing nano bubbles cannot produce a large amount of carbonic gas nano bubbles with so small a diameter as to exert full effects on a human body.

Furthermore, the conventional devices and methods for producing nano bubbles have a problem that, after a medicinal component derived from a galenical or a moisture-retaining component derived from a moisture-retaining agent is dissolved in bath water, the medicinal component or the moisture-retaining component cannot be efficiently absorbed in a living body concurrently with absorption of carbonic gas nano bubbles.

SUMMARY OF THE INVENTION

The present invention was made in view of the foregoing problems. An object of the present invention is to provide a device and a method for increasing blood flow and an insulin-like growth factor with use of a large amount of carbonic gas nano bubbles.

In order to solve the foregoing problems, the device of the present invention for increasing blood flow and an insulin-like growth factor includes: a bathtub; and nano bubble-producing means for producing carbonic gas nano bubbles in bath water in the bathtub.

With the arrangement, the bath water includes carbonic gas nano bubbles with a small particle size. Bubbles with a large diameter move upward in water and at last burst at water surface and vanish. Micro bubbles are minute bubbles with a small diameter, and contract in water until they vanish (completely dissolve). On the other hand, nano bubbles have a diameter further smaller than that of micro bubbles, and can exist in water indefinitely. That is, carbonic gas nano bubbles can exist in bath water stably and for a long time compared with carbonic gas micro bubbles. Therefore, use of carbonic gas nano bubbles allows absorption of a large amount of carbonic gas via skin into a body. Absorption of a large amount of carbonic gas allows increase in blood flow and an insulin-like growth factor.

In order to solve the foregoing problems, the method of the present invention for increasing blood flow and an insulin-like growth factor is arranged so that bath water containing carbonic gas nano bubbles is caused to touch skin.

With the arrangement, the bath water includes carbonic gas nano bubbles with a small particle size. Bubbles with a large diameter move upward in water and at last burst at water surface and vanish. Micro bubbles are minute bubbles with a small diameter, and contract in water until they vanish (completely dissolve). On the other hand, nano bubbles have a diameter further smaller than that of micro bubbles, and can exist in water indefinitely. That is, carbonic gas nano bubbles can exist in bath water stably and for a long time compared with carbonic gas micro bubbles. Therefore, use of carbonic gas nano bubbles allows absorption of a large amount of carbonic gas via skin into a body. Absorption of a large amount of carbonic gas allows increase in blood flow and an insulin-like growth factor.

For a fuller understanding of the nature and advantages of the invention, reference should be made to the ensuing detailed description taken in conjunction with the accompanying drawings.

DESCRIPTION OF THE EMBODIMENTS

The following explains embodiments of the present invention with reference to FIGS. 1 to 16.

Embodiment 1

Figure 1:
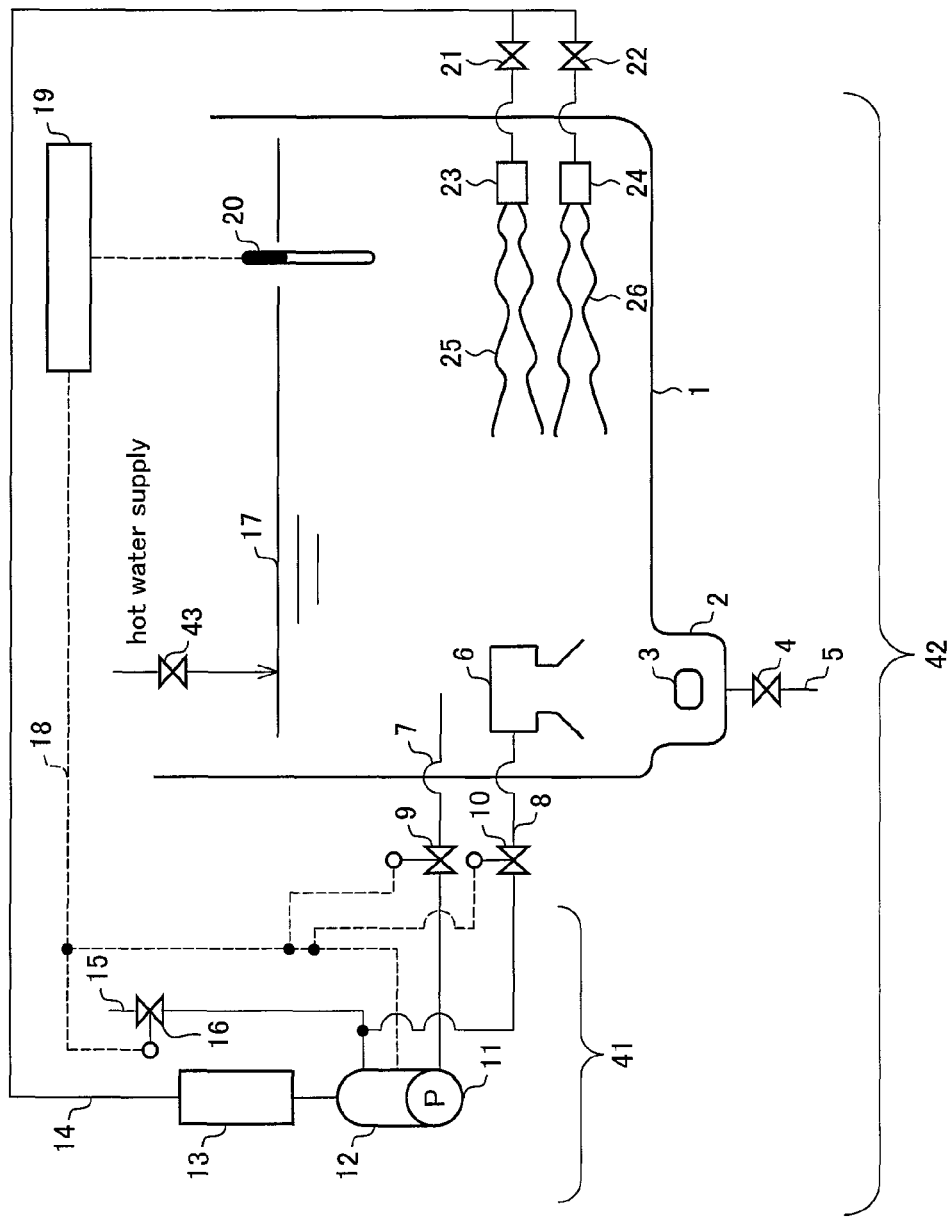
FIG. 1 is a schematic illustrating an embodiment of a device of the present invention for increasing blood flow and an insulin-like growth factor.

FIG. 1 illustrates a device of the present embodiment for increasing blood flow and an insulin-like growth factor.

An increasing device 42 of the present embodiment includes a bathtub 1 and a nano bubble-producing section 41 (nano bubble-producing means). The following explains a mechanism for producing carbonic gas nano bubbles and the increasing device 42 of the present embodiment.

In the device of the present embodiment for increasing blood flow and an insulin-like growth factor, initially, a valve 43 is opened so as to supply bath water into the bathtub 1. When water level of the bathtub 1 reaches a water level 17 that is a water level at a time the bathtub 1 is fully filled with water, the valve 43 is closed so as to stop supplying bath water to the bathtub 1. Temperature of bath water supplied into the bathtub 1 is not particularly limited, and bath water with a suitable temperature may be supplied to the bathtub 1. For example, it is preferable that bath water adjusted to have a temperature of 37 to 42° C. is supplied into the bathtub 1. In order to keep the bath water in the bathtub 1 at a temperature of 37 to 42° C., the increasing device 42 of the present embodiment may additionally include a structure for boiling water.

The bath water supplied into the bathtub 1 can be drained out of the bathtub 1 via a valve 4 and a drainpipe 5 provided in the bathtub 1. That is, in a case of running bath water for the bathtub 1, the valve 4 is closed, and in a case of draining the bath water in the bathtub 1, the valve 4 is opened. When the valve 4 is opened, the bath water in the bathtub 1 is drained via the drainpipe 5.

The bathtub 1 is not particularly limited and may be any bathtub. For example, the bathtub 1 may be a bathtub for home use, medical use, hotel-use, inn-use, or hot spring-use. The size of the bathtub 1 is not particularly limited. For example, the bathtub 1 has a size allowing a whole human body to be put therein, or a size allowing only legs of a human body to be put therein. The material of the bathtub 1 is not particularly limited. For example, the material of the bathtub 1 may be a material such as synthetic resin.

A carbonic gas-bubbling solid agent 3 (carbonic gas-producing means) is put in a container 2. Carbonic gas is emitted from the carbonic gas-bubbling solid agent 3 in contact with bath water. The number of the carbonic gas-bubbling solid agent 3 put in the container 2 is not particularly limited, and the number may be determined suitably according to the amount of carbonic gas nano bubbles required to be produced. For example, in a case where a large amount of carbonic gas nano bubbles are required, a plurality of the carbonic gas-bubbling solid agents 3 may be put in the container 2. More specifically, the number of the carbonic gas-bubbling solid agent 3 put in the container 2 is preferably a number that allows production of carbonic gas of approximately 80 liters per 10 minutes. With the structure, it is possible to produce a large amount of carbonic gas nano bubbles.

The carbonic gas-bubbling solid agent 3 is not particularly limited and may be a publicly known carbonic gas-bubbling solid agent. For example, the carbonic gas-bubbling solid agent 3 may be "Bub®" manufactured by Kao Corporation, but not limited to this. The carbonic gas-bubbling solid agent 3 may be suitably selected in consideration of economy, effect, etc.

The carbonic gas emitted from the carbonic gas-bubbling solid agent 3 is temporarily retained by a carbonic gas-retaining section 6 (carbonic gas-retaining means). The shape and the size of the carbonic gas-retaining section 6 is not particularly limited and may have a shape and a size that allows the carbonic gas-retaining section 6 to efficiently retain carbonic gas emitted from the carbonic gas-bubbling solid agent 3. For example, the carbonic gas-retaining section 6 preferably has a shape that has an opening toward the bottom surface of the bathtub 1. When the carbonic gas-retaining section 6 has the above structure and the container 2 is provided under the carbonic gas-retaining section 6, it is possible for the carbonic gas-retaining section 6 to efficiently retain carbonic gas emitted from the carbonic gas-bubbling solid agent 3.

The carbonic gas retained by the carbonic gas-retaining section 6 is supplied to a nano bubble-producing section 41 via a pipe 8. At that time, the amount of the carbonic gas supplied to the nano bubble-producing section 41 is adjusted by opening/closing of a valve 10 provided in the pipe 8. That is, opening the valve 10 supplies the carbonic gas to the nano bubble-producing section 41. On the other hand, closing the valve 10 stops supplying the carbonic gas to the nano bubble-producing section 41.

The pipe 7 is provided so as to supply a part of the bath water in the bathtub 1 to the nano bubble-producing section 41. At that time, the amount of the bath water supplied to the nano bubble-producing section 41 is adjusted by opening/closing of a valve 9 provided in the pipe 7. That is, opening the valve 9 supplies the bath water to the nano bubble-producing section 41. On the other hand, closing the valve 9 stops supplying the bath water to the nano bubble-producing section 41.

As described above, the carbonic gas and the bath water are supplied to the nano bubble-producing section 41 and carbonic gas nano bubbles are produced using the carbonic gas and the bath water. The following explains a mechanism for producing carbonic gas nano bubbles in the nano bubble-producing section 41.

The nano bubble-producing section 41 includes a gas-liquid mixture-circulating pump 11 (mixing pump), a micro bubble-producing section 12 (first gas-shearing section) and a gas-shearing section 13 (second gas-shearing section).

Initially, carbonic gas is supplied into the micro bubble-producing section 12 via the pipe 8 and bath water is supplied into the micro bubble-producing section 12 via the pipe 7. The carbonic gas and the bath water in the micro bubble-producing section 12 are mixed and sheared by the gas-liquid mixture-circulating pump 11. As a result, carbonic gas micro bubbles (in other words, carbonic gas micro bubble-containing water) are produced.

The gas-liquid mixture-circulating pump 11 may be a well known pump as long as it is a high lift pump. Specifically, the gas-liquid mixture-circulating pump 11 is preferably a high lift pump with lifting height of 40 m or more, i.e. a pump capable of pushing out a gas-liquid mixture with a pressure of 4 $kg/cm^2$ or more. This allows producing a large amount of carbonic gas micro bubbles. Furthermore, the gas-liquid mixture-circulating pump 11 is preferably a pump with two poles. Pumps fall into two types: a pump with two poles and a pump with four poles. The pump with two poles has a more stable torque than the pump with four poles. Therefore, the pump with two poles allows more stable production of a large amount of carbonic gas micro bubbles.

The shape of the micro bubble-producing section 12 is not particularly limited. In order to efficiently produce a rotating sheared flow in the micro bubble-producing section 12, it is preferable that the micro bubble-producing section 12 has a cylindrical flow path. The carbonic gas micro bubble-containing water passes through the flow path.

The carbonic gas and the bath water in the micro bubble-producing section 12 are pressurized by the gas-liquid mixture-circulating pump 11. As a result, a mixed phase swirling flow made of a liquid (bath water) and gas (carbonic gas) is produced in the micro bubble-producing section 12. To be more specific, the gas-liquid mixture-circulating pump 11 is provided with a wing called an impeller, and the impeller is rotated at a high speed to form the mixed-phase swirling flow. At the center of the micro bubble-producing section 12, a gas cavity resulting from high-speed whirling of the mixed-phase swirling flow is formed. The gas cavity is further pressurized by the gas-liquid mixture-circulating pump 11 so as to have an elongated shape resembling a tornado. This allows production of a rotating sheared flow that rotates at a higher speed.

The mixed phase swirling flow is rotated at a high speed while the gas cavity self-supplies gas (e.g. carbonic gas) from the carbonic gas-retaining section 6 to the gas cavity, so that the mixed phase swirling flow is cut and broken. The cutting and the breakage are caused by a difference in rotating speed between gas-liquid mixtures inside and outside the micro bubble-producing section 12.

The speed of rotation of the rotating sheared flow is not particularly limited, but is preferably 500 to 600 rotation/sec. The speed of the rotation of the rotating sheared flow can be set by adjusting the speed of rotation of the wing (impeller). With the above structure, it is possible to produce a large amount of carbonic micro bubbles, finally resulting in production of a large amount of carbonic gas nano bubbles at a nano bubble-discharging nozzle 23 (third gas-shearing section) and a nano bubble-discharging nozzle 24 (third gas-shearing section).

That is, in the micro bubble-producing section 12, a pressure of the gas-liquid mixture is controlled in a fluid mechanical manner so that gas (e.g. carbonic gas) is sucked into an area where a negative pressure is produced, and the gas-liquid mixture is caused by the gas-liquid mixture-circulating pump to move at a high speed so as to further reduce a pressure of the area where the negative pressure is produced, thereby producing micro bubbles. In other words, the bath water and the carbonic gas are caused by the gas-liquid mixture-circulating pump 11 to be efficiently self-supplied, mixed, and dissolved, and the gas-liquid mixture is transferred with pressure, so that micro bubble white-clouded water is produced. Subsequently, the carbonic gas micro bubbles produced by the micro bubble-producing section 12 are transferred with pressure to the gas-shearing section 13 via a pipe. That is, the micro bubble white-clouded water is, while being pressurized, transferred into the gas-shearing section 13. The gas-liquid mixture-circulating pump 11 is a high lift pump. Therefore, when the lifting height is 40 m or more, the gas-liquid mixture-circulating pump 11 can supply the micro bubble white-clouded water into the gas-shearing section 13 with a pressure of 4 kg/cm$^2$ or more.

The shape of the gas-shearing section 13 is not particularly limited, but preferably has a cylindrical flow path so that the rotating sheared flow in the gas-shearing section 13 is made thinner. Furthermore, it is preferable that the flow path of the gas-shearing section 13 has a cylindrical shape whose upper and lower diameters are smaller than a diameter of the flow path of the micro bubble-producing section 12. For example, it is preferable that the cylindrical flow path of the micro bubble-producing section 12 has a circular cross section whose diameter is as follows: a diameter of an opening to discharge the micro bubble white-clouded water is 50 to 80% of a diameter of an opening to absorb a gas-liquid mixture (absorbing opening of the gas-liquid mixture-circulating pump 11). Furthermore, it is preferable that the shape of a cross section of the cylindrical flow path of the gas-shearing section 13 is obtained by downsizing the shape of a cross section of the cylindrical flow path of the micro bubble-producing section 12 by 80% or less.

Furthermore, it is preferable that the inside of the cylindrical flow path of the gas-shearing section 13 (second gas-shearing section) is polished in order to reduce frictional resistance. Furthermore, it is preferable that the flow path is provided with two or more grooves each of 0.3 to 0.6 mm in depth and 0.8 mm or less in width in order to prevent generation of a rotating turbulent flow. Furthermore, it is preferable that a material that forms the flow path of the gas-shearing section 13 has a thickness of 6 to 12 mm in order to prevent a decrease in energy of movement of a fluid that is caused by vibration of the material.

With the structure, the rotating sheared flow produced in the micro bubble-producing section 12 is transferred with pressure to the gas-shearing section 13, allowing the rotating sheared flow to be made thinner in the gas-shearing section 13, and allowing the speed of rotation of the rotating sheared flow to increase. Consequently, it is possible to produce carbonic gas nano bubbles (in other words, carbonic gas nano bubble-containing water) with use of the carbonic gas micro bubbles produced in the micro bubble-producing section 12, and to form a hot spot with extremely high temperature. In the hot spot, heat is generated and free radicals are produced. Because free radicals are more likely to attach to skin, nano bubbles including free radicals are further likely to be absorbed via skin.

As described above, the micro bubble-producing section 12 produces carbonic micro bubbles and the gas-shearing section 13 produces carbonic gas nano bubbles from the carbonic gas micro bubbles.

The carbonic gas nano bubbles produced in the gas-shearing section 13 are supplied to the nano bubble-discharging nozzle 23 (third gas-shearing section) or the nano bubble-discharging nozzle 24 (third gas-shearing section) via a pipe 14. The pipe 14 is provided with valves 21 and 22, and opening/closing of the valves 21 and 22 adjusts the amount of carbonic gas nano bubbles supplied to the nano bubble-discharging nozzles 23 (third gas-shearing section) and 24 (third gas-shearing section), respectively.

The carbonic gas nano bubbles supplied to the nano bubble-discharging nozzle 23 are discharged into the bathtub 1 via a first turbulent flow forming section 25 (turbulent flow forming means). On the other hand, the carbonic gas nano bubbles supplied to the nano bubble-discharging nozzle 24 are discharged into the bathtub 1 via a second turbulent flow forming section 26 (turbulent flow forming means). The shapes of the first turbulent flow forming section 25 and the second turbulent flow forming section 26 are not particularly limited as long as the shapes allow production of turbulent flows including the carbonic gas nano bubbles. The first turbulent flow forming section 25 and the second turbulent flow forming section 26 may have publicly known structures.

As illustrated in FIG. 1, in the device of the present embodiment for increasing blood flow and an insulin-like growth factor, two nano bubble-discharging nozzles are provided. However, the number of the nano bubble-discharging nozzles is not particularly limited, and the number may be determined according to the shape and the size of an object to which carbonic gas nano bubbles are to be jetted. At that time, the number of the turbulent flow forming sections also may be determined according to the number of the nano bubble-discharging nozzles.

In the device of the present embodiment for increasing blood flow and an insulin-like growth factor, a dissolved carbonic gas meter 20 and a dissolved gas-adjusting section 19 are provided. The dissolved carbonic gas meter 20 measures concentration of carbonic gas dissolved in the bath water in the bathtub 1. Information indicative of the concentration of the carbonic gas measured by the dissolved carbonic gas meter 20 is sent to the dissolved carbonic gas-adjusting section 19. In response to the information, the dissolved carbonic gas-adjusting section 19 controls opening/closing of the valve. This allows adjustment of the concentration of the carbonic gas dissolved in the bath water in the bathtub 1. The following explains a method for adjusting concentration of carbonic gas.

Initially, the dissolved carbonic gas meter 20 measures concentration of carbonic gas dissolved in the bath water in the bathtub 1. The dissolved carbonic gas meter 20 is not particularly limited and may be a well known carbonic gas meter. A result of the measurement by the dissolved carbonic gas meter 20 is sent to the dissolved carbonic gas-adjusting section 19. In the dissolved carbonic gas-adjusting section 19, concentration of carbonic gas to be dissolved in the bath water in the bathtub 1 is set beforehand (preset value). When the concentration of the carbonic gas measured by the dissolved carbonic gas meter 20 is not less than the preset value, the dissolved carbonic gas-adjusting section 19 causes a valve to operate so that the amount of the carbonic gas nano bubbles in the bath water in the bathtub 1 drops. When the concentration of the carbonic gas measured by the dissolved carbonic gas meter 20 is less than the preset value, the dissolved carbonic gas-adjusting section 19 causes the valve to operate so that the amount of the carbonic gas nano bubbles in the bath water in the bathtub 1 increases.

The preset value is not particularly limited and may be set suitably. Preferable example of the preset value is 1000 ppm. The preset value being 1000 ppm allows carbonic gas nano bubbles to be efficiently absorbed via skin. This allows increasing the blood flow and the amount of insulin-like growth factor.

Specifically, when the concentration of the carbonic gas measured by the dissolved carbonic gas meter 20 is not less than the preset value, the dissolved carbonic gas-adjusting section 19 opens the valves 16 and 9 and closes the valve 10 via a signal line 18. Consequently, the bath water and air are supplied to the micro bubble-producing section 12 via the pipe 7 and a pipe 15, respectively. The pipe 15 is provided so as to supply gas other than carbonic gas (e.g. air in a bath room) to the micro bubble-producing section 12. At that time, nano bubbles produced in the gas-shearing section 13 does not contain carbonic acid, and therefore the concentration of the carbonic gas dissolved in the hot water in the bathtub 1 drops to the preset concentration.

On the other hand, when the concentration of the carbonic gas measured by the dissolved carbonic gas meter 20 is less than the preset value, the dissolved carbonic gas-adjusting section 19 opens the valves 9 and 10 and closes the valve 16 via the signal line 18. Consequently, the bath water and carbonic gas are supplied to the micro bubble-producing section 12 via the pipes 7 and 8, respectively. At that time, carbonic gas nano bubbles are produced in the gas-shearing section 13, and therefore the concentration of the carbonic gas dissolved in the bath water in the bathtub 1 increases up to the preset concentration. As described above, the concentration of the carbonic gas dissolved in the hot water in the bathtub 1 can be adjusted to be a desired value.

The gas-liquid mixture-circulating pump 11, the micro bubble-producing section 12, the gas-shearing section 13, the valve 16 (needle valve), the nano bubble-discharging nozzle 23 (third gas-shearing section) and the nano bubble-discharging nozzle 24 (third gas-shearing section) that constitute the nano bubble-producing section 41 may be commercially available ones. Specifically, they may be products of Kyowakisetsu K. K. (such as BUVITAS HYK).

Figure 2:
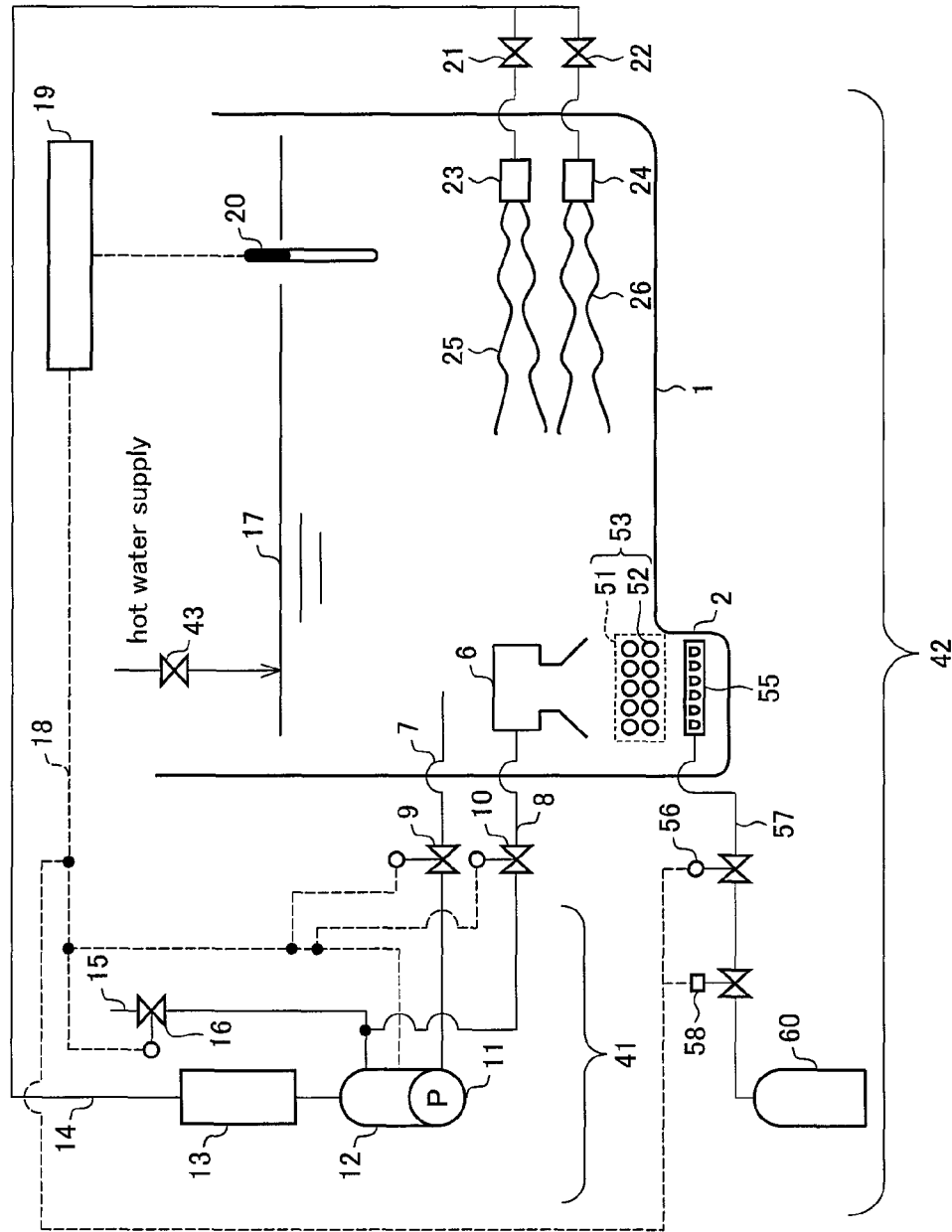
FIG. 2 is a schematic illustrating another embodiment of a device of the present invention for increasing blood flow and an insulin-like growth factor.

Furthermore, as illustrated in FIG. 2, the device of the present embodiment for increasing blood flow and an insulin-like growth factor may be arranged so that the carbonic gas-bubbling solid agent 3 is replaced with a liquid carbonic gas container 60 (carbonic gas-producing means) and a radium ion-dissolving section 53 is provided above the container 2. The following explains this arrangement.

The liquid carbonic gas container 60 is connected with an air-diffusing pipe 55 via a pipe 57. The pipe 57 is provided with valves 56 and 58, and the valves 56 and 58 adjust the amount of carbonic gas discharged from the air-diffusing pipe 55. The air-diffusing pipe 55 is provided in the container 2, and the radium ion-dissolving section 53 is provided above the air-diffusing pipe 55.

The liquid carbonic gas container 60 contains carbonic gas. The carbonic gas is discharged from the air-diffusing pipe 55 via the pipe 57 and the valve 56, by a negative pressure generated by the valve 58 serving as a pressure-reducing valve.

The dissolved carbonic gas-adjusting section 19 adjusts opening/closing of the valve 56. Opening/closing the valve 56 allows adjustment of concentration of carbonic gas dissolved in the bath water in the bathtub 1.

Specifically, when the concentration of the carbonic gas measured by the dissolved carbonic gas meter 20 is not less than the preset value, the dissolved carbonic gas-adjusting section 19 closes the valve 56 via the signal line 18. Consequently, it is possible to reduce the amount of carbonic gas supplied from the air-diffusing pipe 55 to the carbonic gas-retaining section 6, and to reduce the concentration of the carbonic gas dissolved in the bath water in the bathtub 1 to the preset concentration.

On the other hand, when the concentration of the carbonic gas measured by the dissolved carbonic gas meter 20 is less than the preset value, the dissolved carbonic gas-adjusting section 19 opens the valve 56 via the signal line 18. Consequently, it is possible to increase the amount of carbonic gas supplied from the air-diffusing pipe 55 to the carbonic gas-retaining section 6, and to increase the concentration of the carbonic gas dissolved in the bath water in the bathtub 1 up to the preset concentration.

Opening/closing of the valve 56 may be controlled in accordance with opening/closing of the valves 9, 10, and 16. Specifically, when the concentration of the carbonic gas measured by the dissolved carbonic gas meter 20 is not less than the preset value, the dissolved carbonic gas-adjusting section 19 opens the valves 16 and 9 and closes the valves 10 and 56 via the signal line 18. Consequently, it is possible to drop the concentration of the carbonic gas dissolved in the bath water in the bathtub 1 to the preset concentration. On the other hand, when the concentration of the carbonic gas measured by the dissolved carbonic gas meter 20 is less than the preset value, the dissolved carbonic gas-adjusting section 19 opens the valves 9, 10, and 56 and closes the valve 16 via the signal line 18. Consequently, it is possible to increase the concentration of the carbonic gas dissolved in the bath water in the bathtub 1 up to the preset concentration.

The radium ion-dissolving section 53 includes a container 51 and a radium ore 52 contained in the container 51.

The container 51 is not particularly limited as long as it is capable of containing the radium ore 52. It is preferable that the container 51 has a structure in which carbonic gas discharged from the air-diffusing pipe 55 provided below the container 51 is in full contact with the radium ore 52 and as a result radium ions dissolve easily in the bath water. For example, the container 51 is preferably a container that is made of resin or stainless steel and that has many openings connecting the inside and the outside of the container.

The radium ore 52 is not particularly limited, and may be a radium ore that exists in the natural world and that irradiates a radioactive ray. The shape or properties etc. of the radium ore 52 are not particularly limited too and may be suitably selected according to price and origin. Specific examples of the radium ore 52 include "Radium Ball®" manufactured by Ohbakudo K. K., "Tamagawa no Kouseki®" manufactured by Moose K. K., and "Radium Kenkou no Yu®" manufactured by NST. Co., Ltd.

The amount of radium included in the radium ore 52 may be measured by "Radi®" manufactured by Horiba Ltd. for example. Therefore, a radium ore capable of irradiating a suitable radioactive ray may be used as the radium ore 52.

For example, when a radium ball of approximately 1 cm in diameter is used as the radium ore 52, the radium ore 52 can irradiate a radioactive ray of 0.601 micro sievert per hour. Tamagawa Spring in Akita prefecture, which is famous as a hot spring with a medicinal effect, contains radium, and the radium irradiates a radioactive ray of 0.734 micro sievert per hour. With the above structure, it is possible to irradiate a radioactive ray with an amount similar to that of the radioactive ray of the hot spring with a medicinal effect. Unlike other hot springs, Tamagawa Spring in Akita prefecture is a hot spring for a medical treatment and rest. Tamagawa Spring in Akita prefecture exists deep in mountains and therefore is not open during winter. However, with the device of the present embodiment for increasing blood flow and an insulin-like growth factor, it is easy to make a medical treatment using carbonic gas nano bubbles regardless of the seasons.

The following explains another embodiments of the device of the present invention for increasing blood flow and an insulin-like growth factor. The same structures as those in Embodiment 1 are given the same reference numerals and detailed explanations thereof are omitted here.

Embodiment 2

The device of the present embodiment for increasing blood flow and an insulin-like growth factor is the same as the structure of Embodiment 1 except that the device of the present embodiment includes a pH meter 28 and a pH adjusting section 27.

Figure 3:
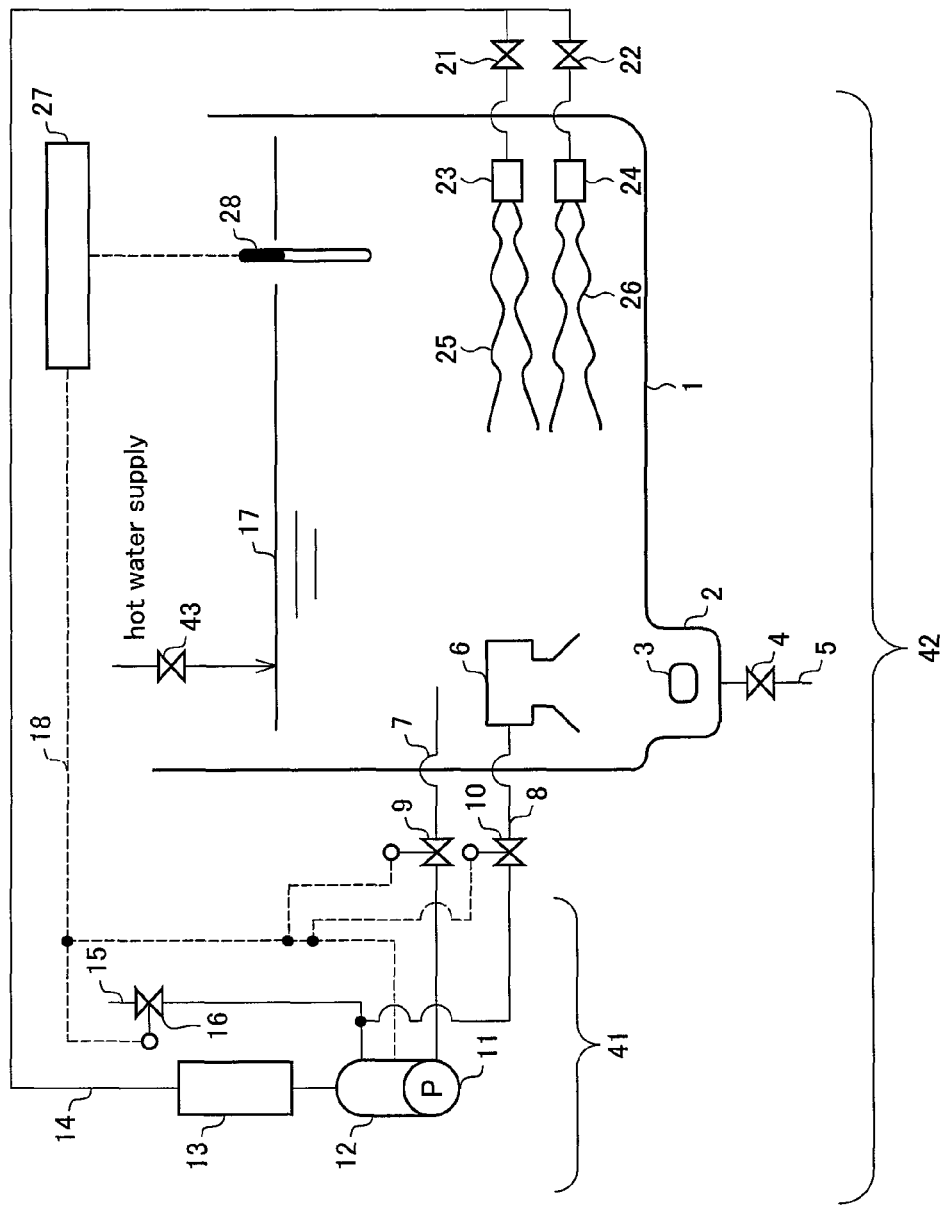
FIG. 3 is a schematic illustrating still another embodiment of a device of the present invention for increasing blood flow and an insulin-like growth factor.
Figure 4:
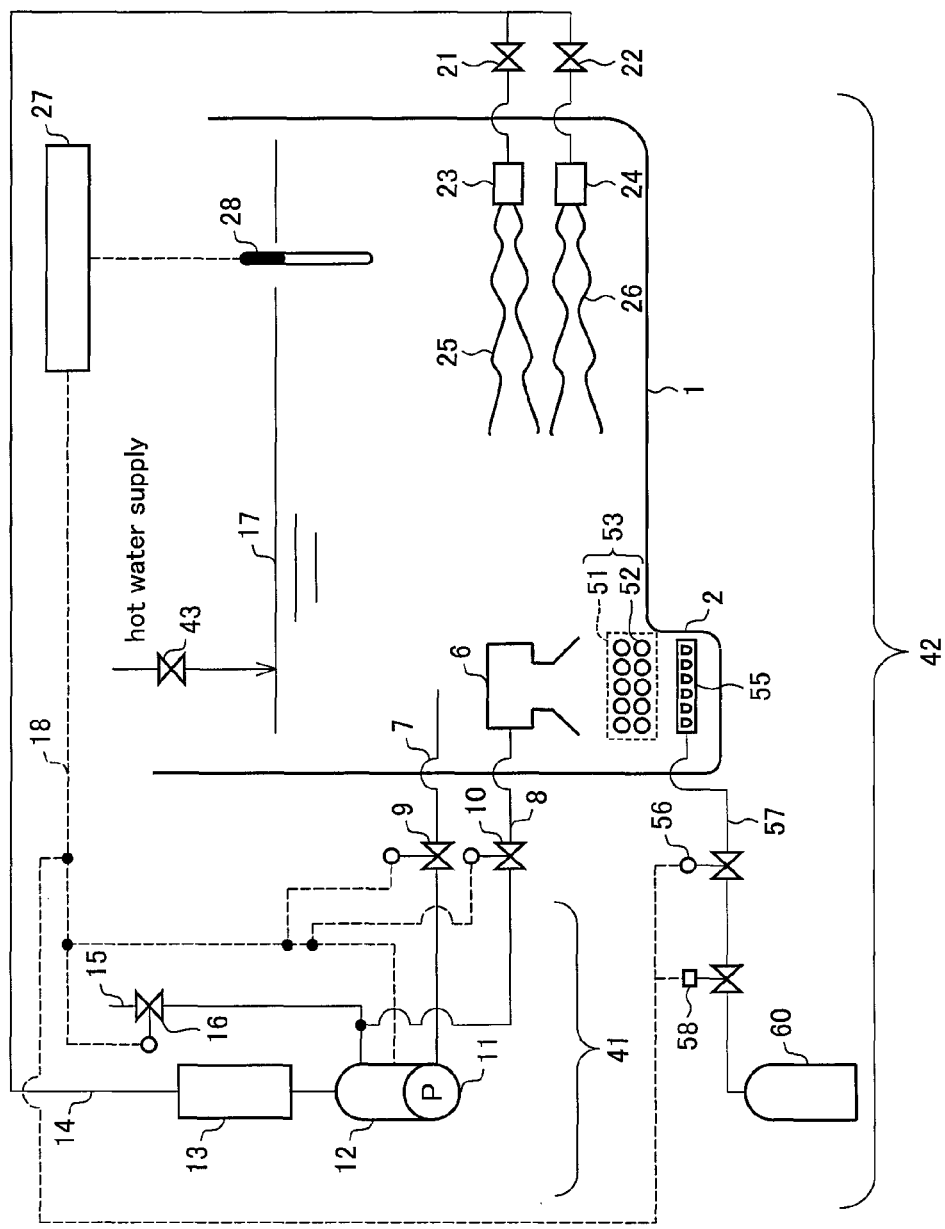
FIG. 4 is a schematic illustrating still another embodiment of a device of the present invention for increasing blood flow and an insulin-like growth factor.

Specifically, as illustrated in FIGS. 3 and 4, the device of the present embodiment for increasing blood flow and an insulin-like growth factor includes the pH adjusting section 27 instead of the dissolved carbonic gas-adjusting section 19, and includes the pH meter 28 instead of the dissolved carbonic gas meter 20.

As concentration of carbonic gas dissolved in bath water in the bathtub 1 is higher, pH of the bath water is lower. Accordingly, use of the pH meter 28 allows detection of the concentration of carbonic gas dissolved in bath water in the bathtub 1.

The pH meter 28 is not particularly limited and may be a publicly known pH meter. As described above, it is known that the concentration of carbonic gas dissolved in bath water in the bathtub 1 has a correlation with pH of the bath water. Accordingly, by preparing data indicative of the correlation beforehand and storing the data in the pH adjusting section 27, it is possible to adjust the concentration of the dissolved carbonic gas according to pH of the bath water. The data indicative of the correlation may be obtained from an experiment carried out with a well known method.

The pH adjusting section 27 adjusts the concentration of carbonic gas dissolved in bath water in the bathtub 1 according to pH of the bath water, i.e. the concentration of the dissolved carbonic gas. At that time, the pH adjusting section 27 adjusts the concentration of the carbonic gas dissolved in the bath water in the bathtub 1 by opening/closing the valves 9, 10, 16, and 56. The opening/closing of the valves has been already explained in Embodiment 1 and therefore explanation thereof is omitted here.

Embodiment 3

The device of the present embodiment for increasing blood flow and an insulin-like growth factor is the same as the device of Embodiment 1 except that the number of a nano bubble-discharging nozzle is one and the turbulent flow forming section is deleted in the device of the present embodiment.

Figure 5:
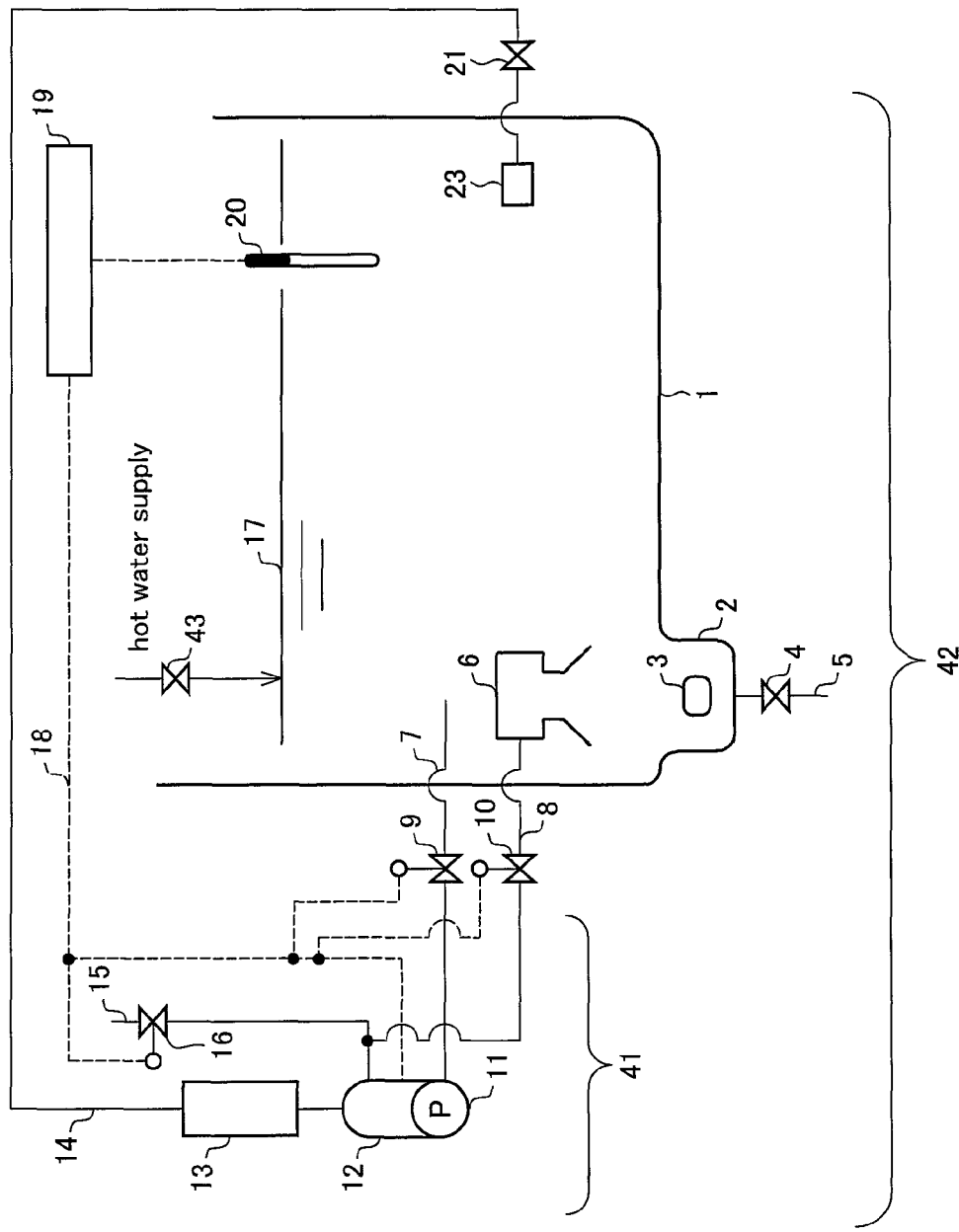
FIG. 5 is a schematic illustrating still another embodiment of a device of the present invention for increasing blood flow and an insulin-like growth factor.
Figure 6:
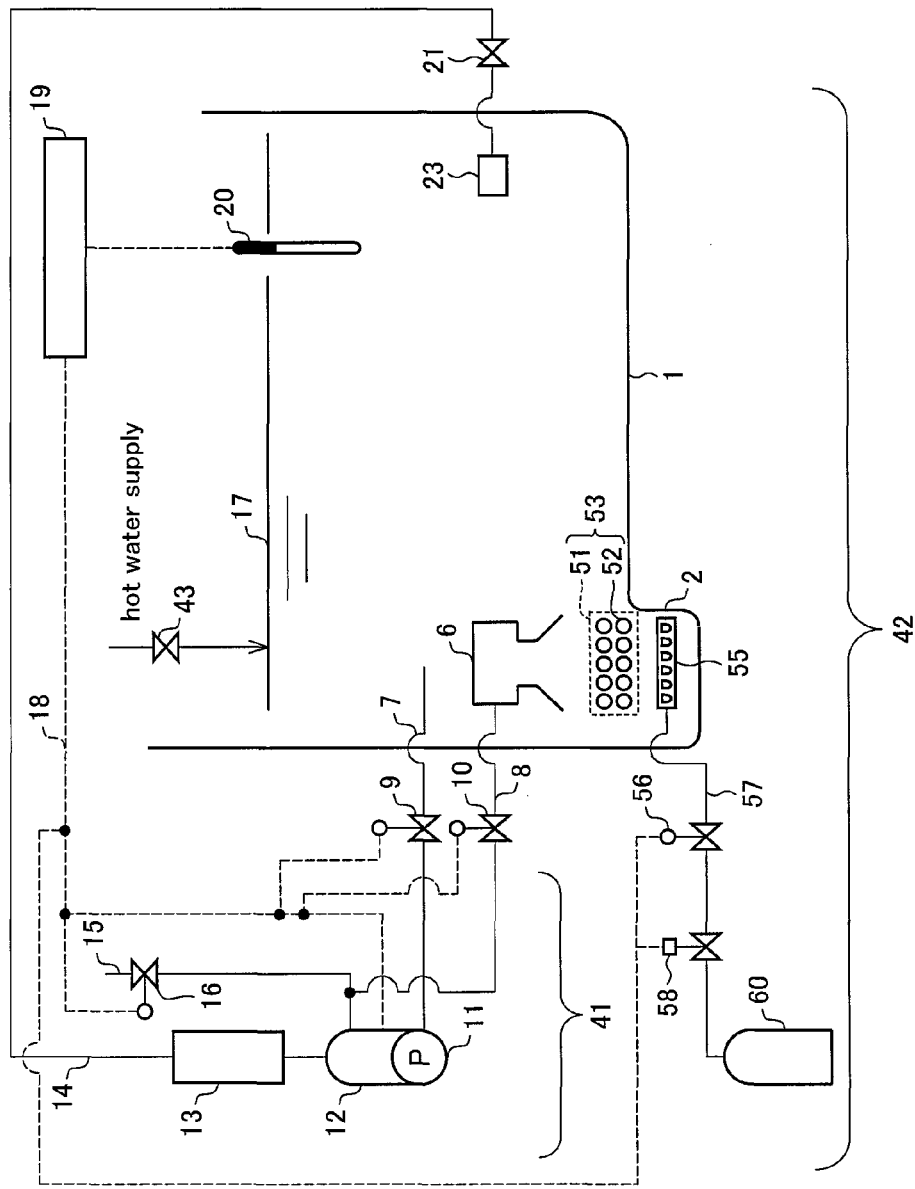
FIG. 6 is a schematic illustrating still another embodiment of a device of the present invention for increasing blood flow and an insulin-like growth factor.

Specifically, as illustrated in FIGS. 5 and 6, in the device of the present embodiment for increasing blood flow and an insulin-like growth factor, carbonic gas nano bubbles produced in the nano bubble-producing section 41 are discharged from only one nozzle (nano bubble-discharging nozzle 23) into the bathtub 1 and pervade the bathtub 1.

Therefore, with the above structure, it is possible to simplify the structure of the increasing device 42. Furthermore, with the above structure, bathing enables a whole body to absorb carbonic gas nano bubbles, resulting in increase in blood flow and an insulin-like growth factor.

Embodiment 4

Figure 7:
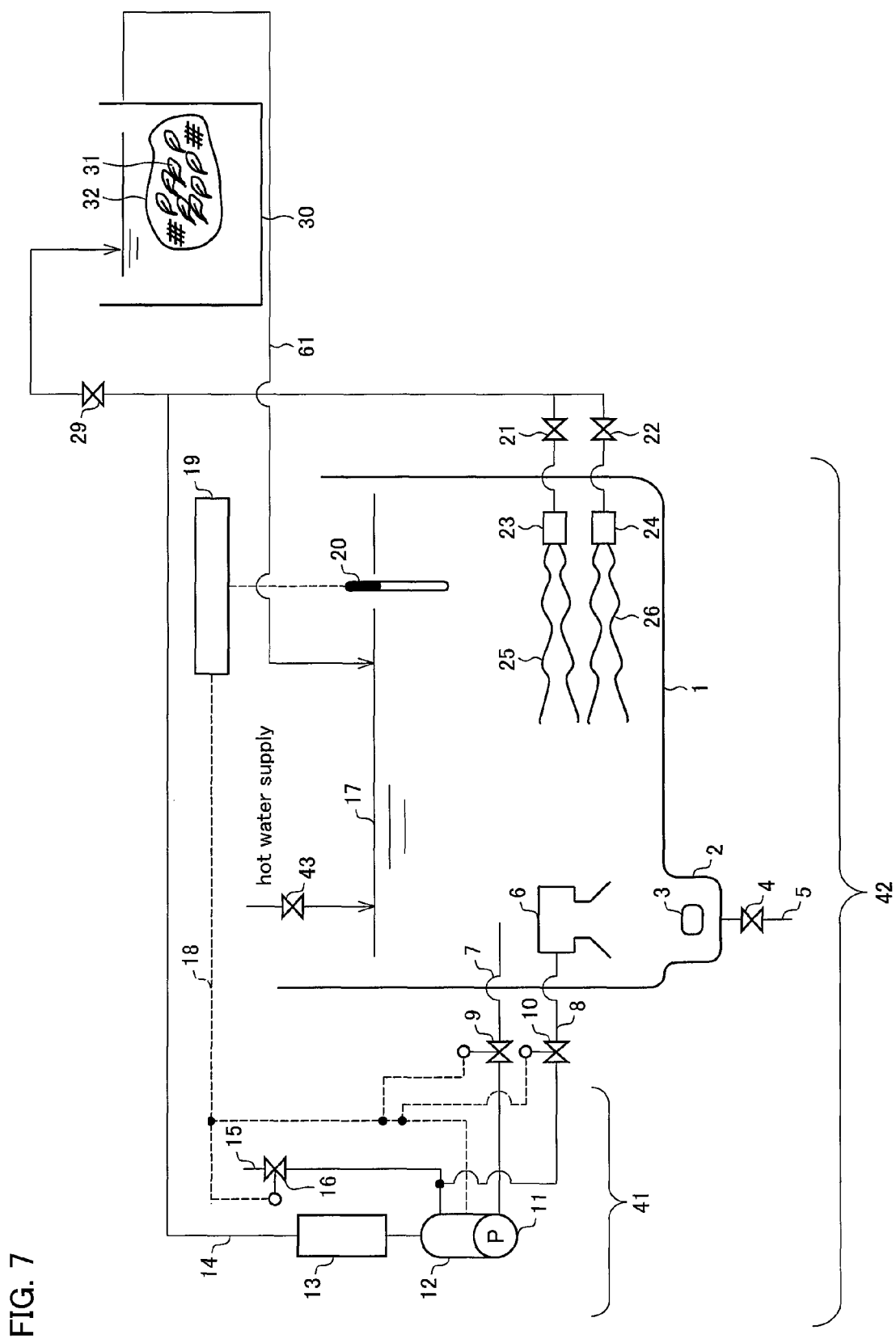
FIG. 7 is a schematic illustrating still another embodiment of a device of the present invention for increasing blood flow and an insulin-like growth factor.
Figure 8:
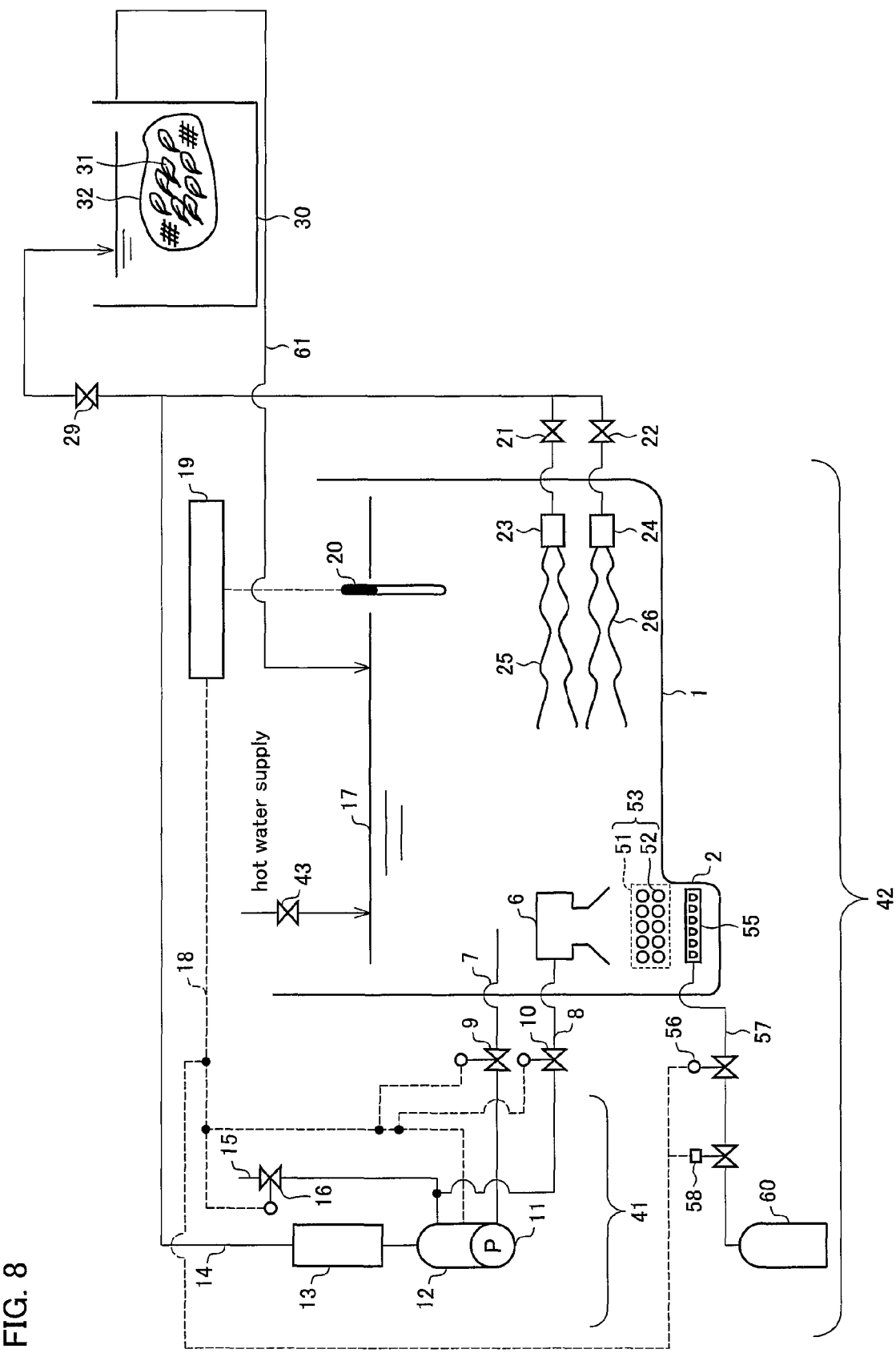
FIG. 8 is a schematic illustrating still another embodiment of a device of the present invention for increasing blood flow and an insulin-like growth factor.

As illustrated in FIGS. 7 and 8, the device of the present embodiment for increasing blood flow and an insulin-like growth factor is the same as the structure of Embodiment 1 except that the device of the present embodiment includes an extraction tank 30 that includes a container 32 filled with a galenical 31.

The position where the extraction tank 30 is provided is not particularly limited, but is preferably outside of the bathtub 1. With the above structure, the extraction tank 30 is provided separately and outside the bathtub 1, so that efficiency in extracting a medicinal component is high. There is a possibility that a condition under which the efficiency in extracting a medicinal component is the highest is harmful to a human body (for example, an extraction of a medicinal component at a high temperature). However, separately providing the bathtub 1 and the extraction tank 30 allows setting a condition in the bathtub 1 to be optimal for a human body and setting a condition in the extraction tank 30 to be optimal for extraction of a medicinal component. This enhances the effect of increasing blood flow and an insulin-like growth factor.

The shape of the container 32 is not particularly limited as long as the shape facilitates extraction of a medicinal component of the galenical 31. A preferable example of the shape of the container 32 is a meshed bag.

The galenical 31 to be contained in the container 32 is not particularly limited, and may be a publicly known galenical according to purposes. For example, it is preferable that the galenical 31 is at least one selected from the group consisting of calamus, citron, Angelica acutiloba, camomile, Cnidium officimale, dried orange peel, carrot, fennel, Scutellaria baicalensis, phellodendron bark, spruce, aloe, ginger, sweetroot, and cinnamon.

Specifically, as illustrated in FIGS. 7 and 8, in the device of the present embodiment for increasing blood flow and an insulin-like growth factor, a valve 29 is opened and the valves 21 and 22 are closed. Consequently, hot water including carbonic gas nano bubbles produced in the nano bubble-producing section 41 is supplied into the extraction tank 30. In the extraction tank 30, a medicinal component is extracted from the galenical 31 into the hot water including the carbonic gas nano bubbles. The hot water including the medicinal component and the carbonic gas nano bubbles is supplied to the bathtub 1 via a pipe 61.

With the structure, when the carbonic gas nano bubbles are absorbed via skin, the medicinal component is absorbed via skin at the same time. The medicinal component absorbed via skin is taken into capillaries, and thus circulates through and diffuses into a whole body. Consequently, a pharmacological effect is exerted on the whole body. Conventionally, a common method for diffusing a medicinal component of a pharmaceutical product into a whole body has been oral ingestion, injection etc. However, with the device of the present embodiment for increasing blood flow and an insulin-like growth factor, both of the medicinal component and the carbonic gas nano bubbles can be absorbed via skin under a condition where the carbonic gas nano bubbles are likely to be absorbed.

Embodiment 5

Figure 9:
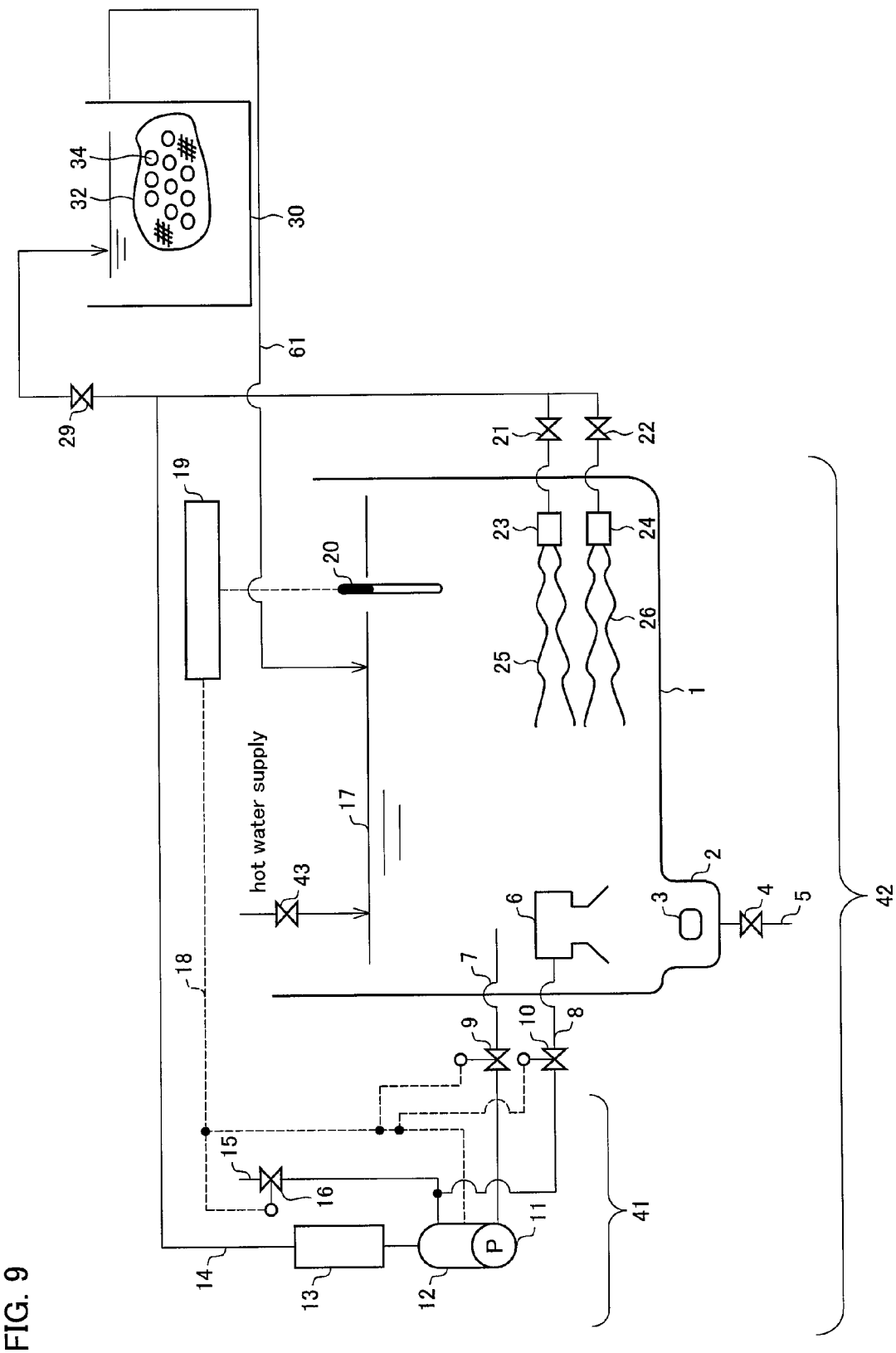
FIG. 9 is a schematic illustrating still another embodiment of a device of the present invention for increasing blood flow and an insulin-like growth factor.
Figure 10:
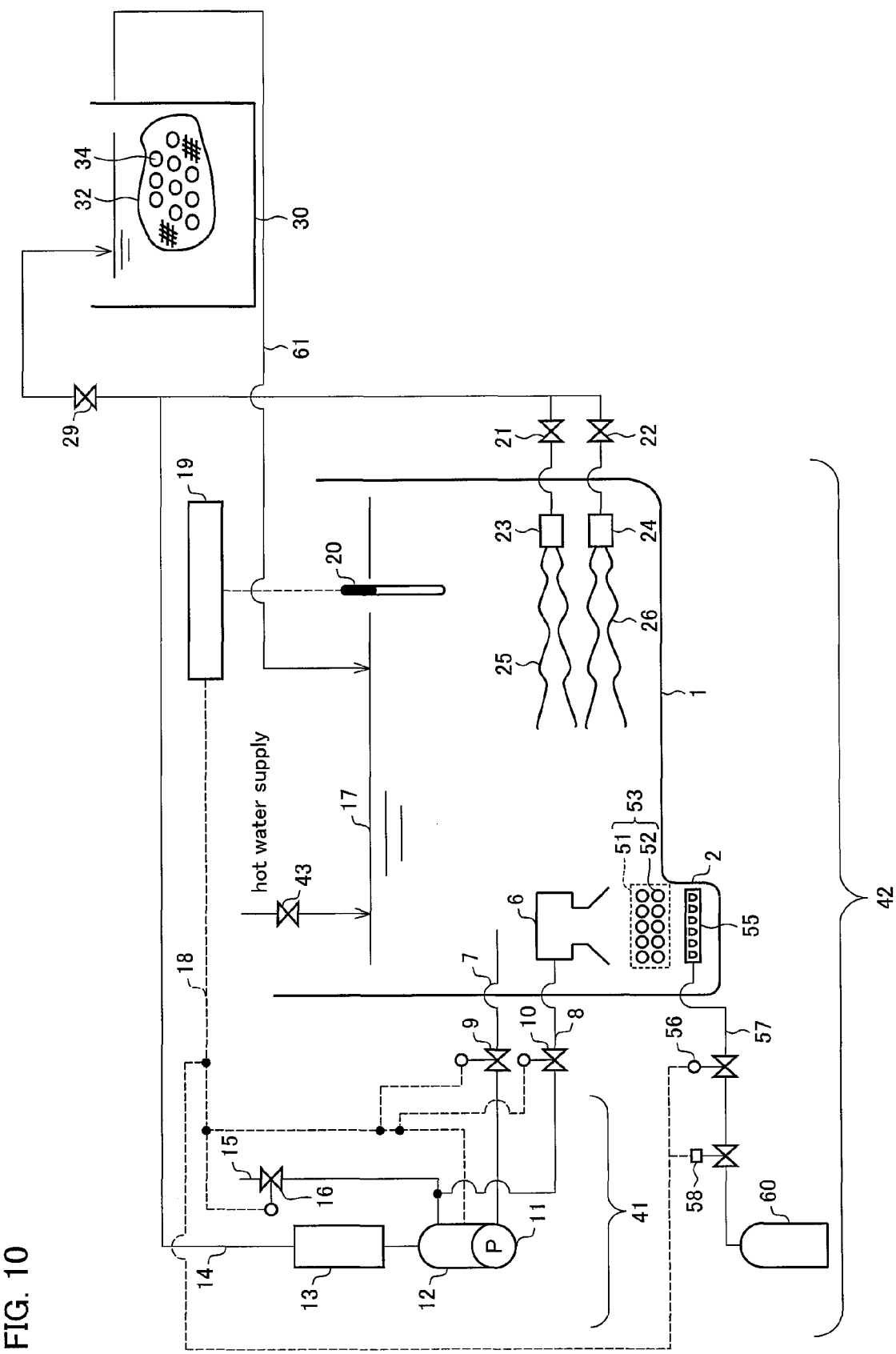
FIG. 10 is a schematic illustrating still another embodiment of a device of the present invention for increasing blood flow and an insulin-like growth factor.

As illustrated in FIGS. 9 and 10, the device of the present embodiment for increasing blood flow and an insulin-like growth factor is the same as the structure of Embodiment 1 except that the device of the present embodiment includes an extraction tank 30 that includes a container 32 filled with a moisture-retaining agent 34.

The position where the extraction tank 30 is provided is not particularly limited, but is preferably outside of the bathtub 1. With the above structure, the extraction tank 30 is provided separately and outside the bathtub 1, so that efficiency in extracting a moisture-retaining component is high. There is a possibility that a condition under which the efficiency in extracting a moisture-retaining component is the highest is harmful to a human body (for example, an extraction of a moisture-retaining component at a high temperature). However, separately providing the bathtub 1 and the extraction tank 30 allows setting a condition in the bathtub 1 to be optimal for a human body and setting a condition in the extraction tank 30 to be optimal for extraction of a moisture-retaining component. This enhances the effect of increasing blood flow and an insulin-like growth factor.

The shape of the container 32 is not particularly limited as long as the shape facilitates extraction of a moisture-retaining component of the moisture-retaining agent 34. A preferable example of the shape of the container 32 is a meshed bag.

The moisture-retaining agent 34 to be contained in the container 32 is not particularly limited, and may be a publicly known moisture-retaining agent according to purposes. For example, it is preferable that the moisture-retaining agent 34 is at least one selected from the group consisting of seaweed, a fruit, liquid lanoline, glycerin, casein, olive oil, soy oil, paraffin, Vaseline, propylene glycol, and honey.

Specifically, as illustrated in FIGS. 9 and 10, in the device of the present embodiment for increasing blood flow and an insulin-like growth factor, a valve 29 is opened and the valves 21 and 22 are closed. Consequently, hot water including carbonic gas nano bubbles produced in the nano bubble-producing section 41 is supplied into the extraction tank 30. In the extraction tank 30, a moisture-retaining component is extracted from the moisture-retaining agent 34 into the hot water including the carbonic gas nano bubbles. The hot water including the moisture-retaining component and the carbonic gas nano bubbles is supplied to the bathtub 1 via a pipe 61.

With the structure, when the carbonic gas nano bubbles are absorbed via skin, the moisture-retaining component is absorbed via skin at the same time. The moisture-retaining component absorbed via skin is taken into capillaries, and thus circulates through and diffuses into a whole body. Consequently, a moisture retention effect is exerted on the whole body. Conventionally, a common method for diffusing a moisture-retaining component of a moisture-retaining agent into a whole body has been oral ingestion, injection etc. However, with the device of the present embodiment for increasing blood flow and an insulin-like growth factor, both of the moisture-retaining component and the carbonic gas nano bubbles can be absorbed via skin under a condition where the carbonic gas nano bubbles are likely to be absorbed.

Embodiment 6

The device of the present embodiment for increasing blood flow and an insulin-like growth factor is the same as the structure of Embodiment 4 or 5 except that the device of the present embodiment further includes a diffusion pipe 35.

Figure 11:
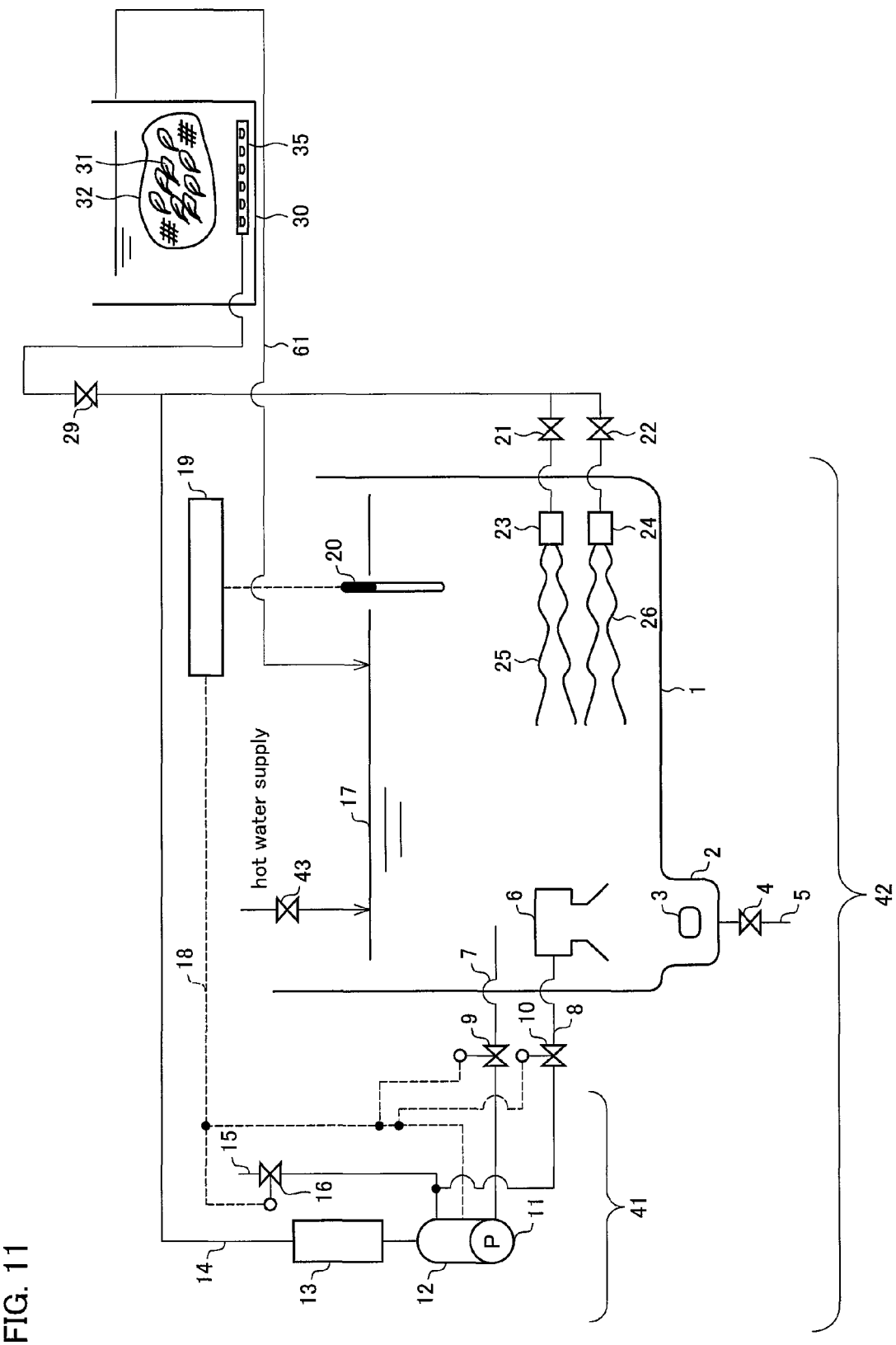
FIG. 11 is a schematic illustrating still another embodiment of a device of the present invention for increasing blood flow and an insulin-like growth factor.
Figure 12:
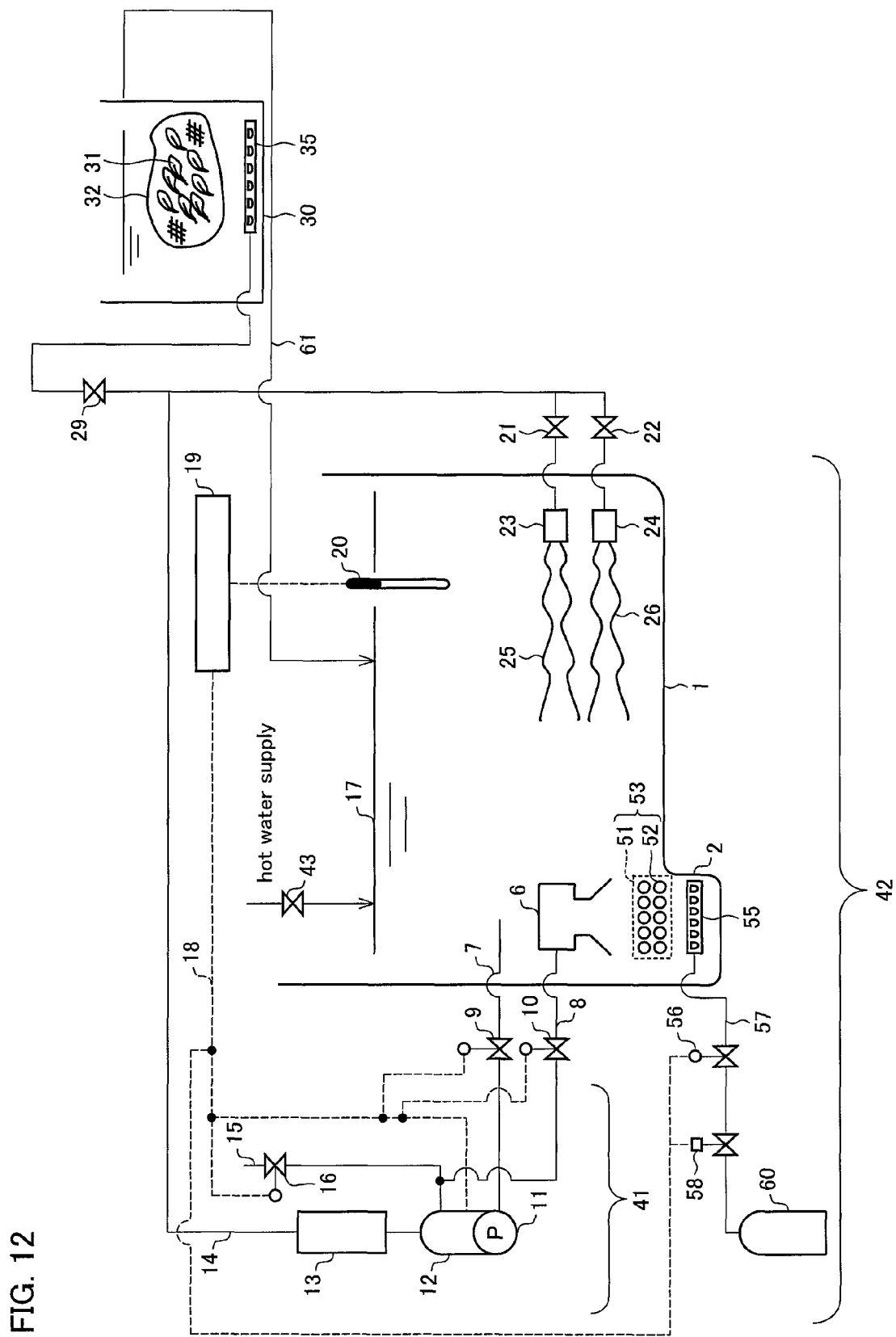
FIG. 12 is a schematic illustrating still another embodiment of a device of the present invention for increasing blood flow and an insulin-like growth factor.

As illustrated in FIGS. 11 and 12, the device of the present embodiment for increasing blood flow and an insulin-like growth factor includes the diffusion pipe 35 under the container 32 explained in Embodiment 4 or 5. The diffusion pipe 35 is connected with the pipe 14 via the valve 29. In the device of the present embodiment for increasing blood flow and an insulin-like growth factor, when the valve 29 is opened and the valves 21 and 22 are closed, bath water including carbonic gas nano bubbles produced in the nano bubble-producing section 41 is discharged toward the container 32 in the extraction tank 30. Since the container 32 contains the galenical 31, the above structure allows efficient extraction of a medicinal component. That is, washing ability of carbonic gas nano bubbles allows efficient extraction of the medicinal component.

The position of the diffusion pipe 35 is not particularly limited, but is preferably a position that allows carbonic gas nano bubbles to be jetted out directly toward the container 32. Such position allows further efficient extraction of the medicinal component.

Hot water including the carbonic gas nano bubbles with a large amount of the medicinal component is supplied to the bathtub 1 via the pipe 61.

With the structure, when the carbonic gas nano bubbles are absorbed via skin, a larger amount of the medicinal component is absorbed via skin at the same time. The medicinal component absorbed via skin is taken into capillaries, and thus circulates through and diffuses into a whole body. Consequently, a pharmaceutical effect can be exerted on the whole body.

Embodiment 7

The device of the present embodiment for increasing blood flow and an insulin-like growth factor is the same as the structure of Embodiment 6 except that the device of the present embodiment further includes a heater 36.

The heater 36 is provided in the extraction tank 30. The heater 36 heats bath water in the extraction tank 30, and as a result the galenical 31 or the moisture-retaining agent 34 contained in the container 32 is heated. Since the galenical 31 or the moisture-retaining agent 34 is heated, it is possible to more efficiently extract a medicinal component or a moisture-retaining component included in the galenical 31 or the moisture-retaining agent 34.

Figure 13:
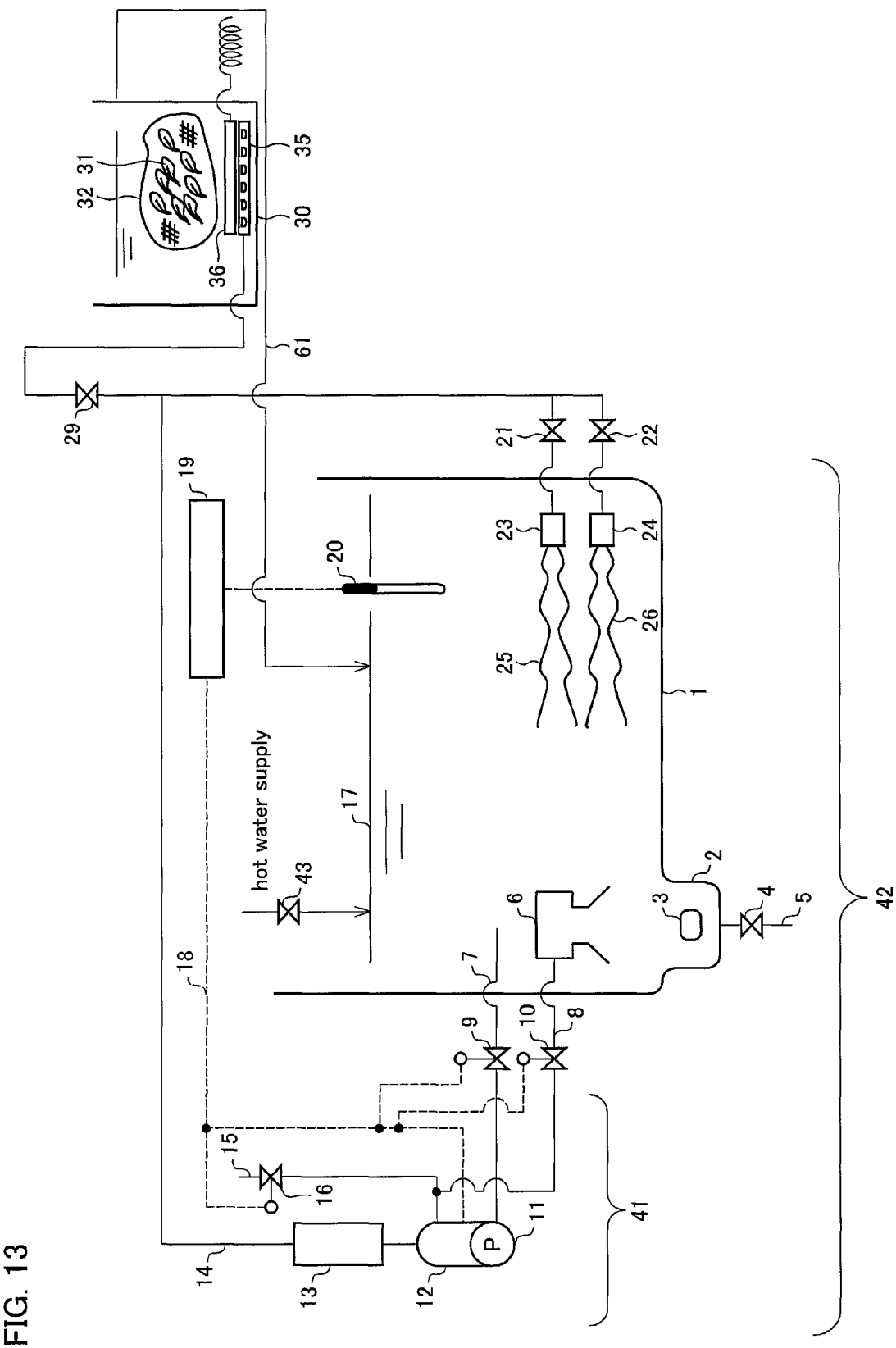
FIG. 13 is a schematic illustrating still another embodiment of a device of the present invention for increasing blood flow and an insulin-like growth factor.
Figure 14:
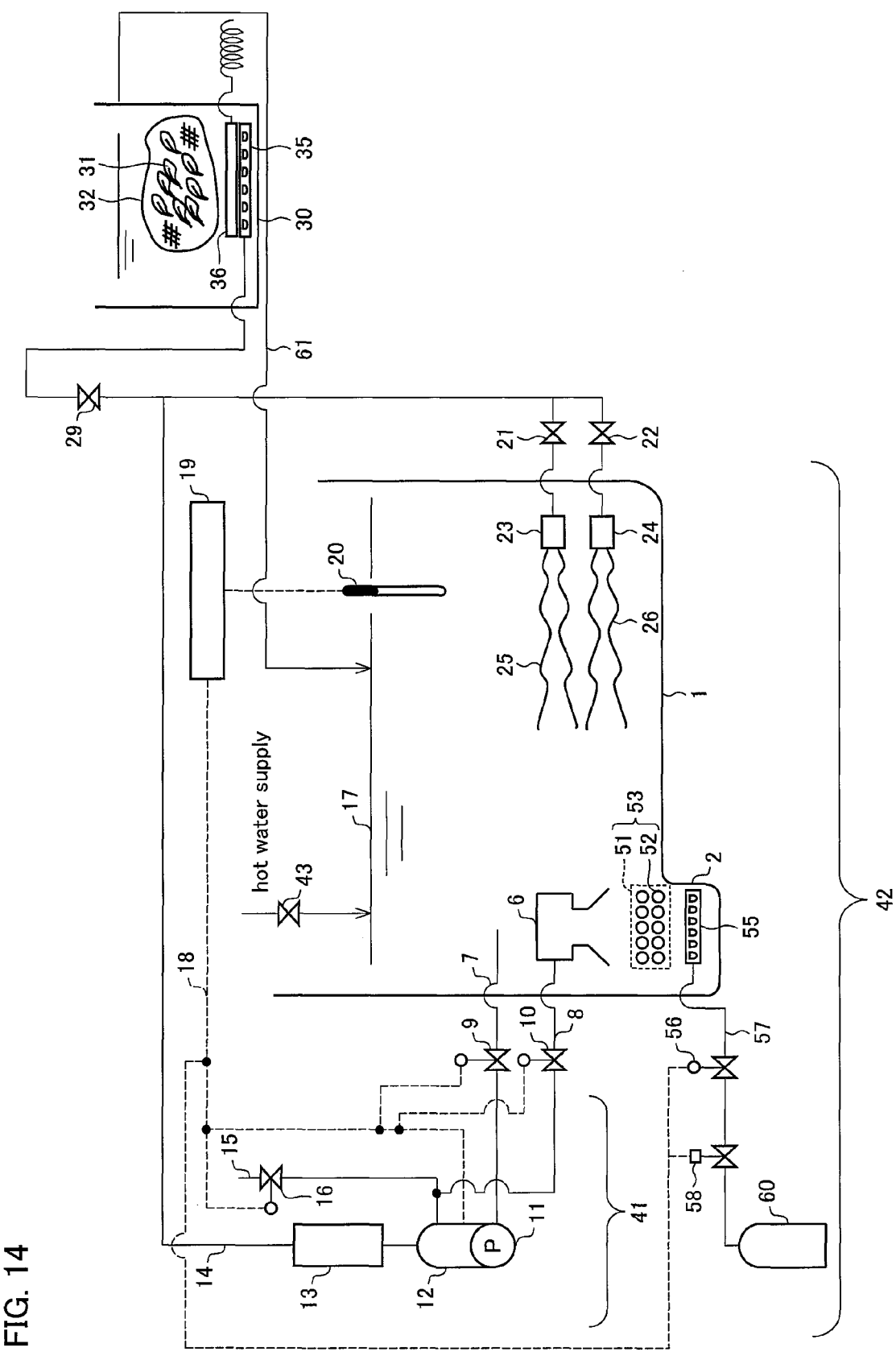
FIG. 14 is a schematic illustrating still another embodiment of a device of the present invention for increasing blood flow and an insulin-like growth factor.

The heater 36 is not particularly limited and may be a publicly known heater. The position where the heater 36 is provided is not particularly limited, and may be a position that allows the heater 36 to heat the bath water in the extraction tank 30. For example, as illustrated in FIGS. 13 and 14, it is preferable that, in the device of the present embodiment for increasing blood flow and an insulin-like growth factor, the heater 36 is provided above the diffusion pipe 35 explained in Embodiment 6 and below the container 32.

Hot water including the carbonic gas nano bubbles with a large amount of the medicinal component or moisture-retaining component is supplied to the bathtub 1 via the pipe 61.

With the structure, when the carbonic gas nano bubbles are absorbed via skin, a larger amount of the medicinal component or the moisture-retaining component is absorbed via skin at the same time. The medicinal component or the moisture-retaining component absorbed via skin is taken into capillaries, and thus circulates through and diffuses into a whole body. Consequently, a pharmaceutical effect or a moisture retention effect can be exerted on the whole body.

Embodiment 8

The device of the present embodiment for increasing blood flow and an insulin-like growth factor is the same as the structure of Embodiment 7 except that the device of the present embodiment further includes a first temperature-adjusting section 37, a thermometer 38, a thermometer 39, and a second temperature-adjusting section 40.

Figure 15:
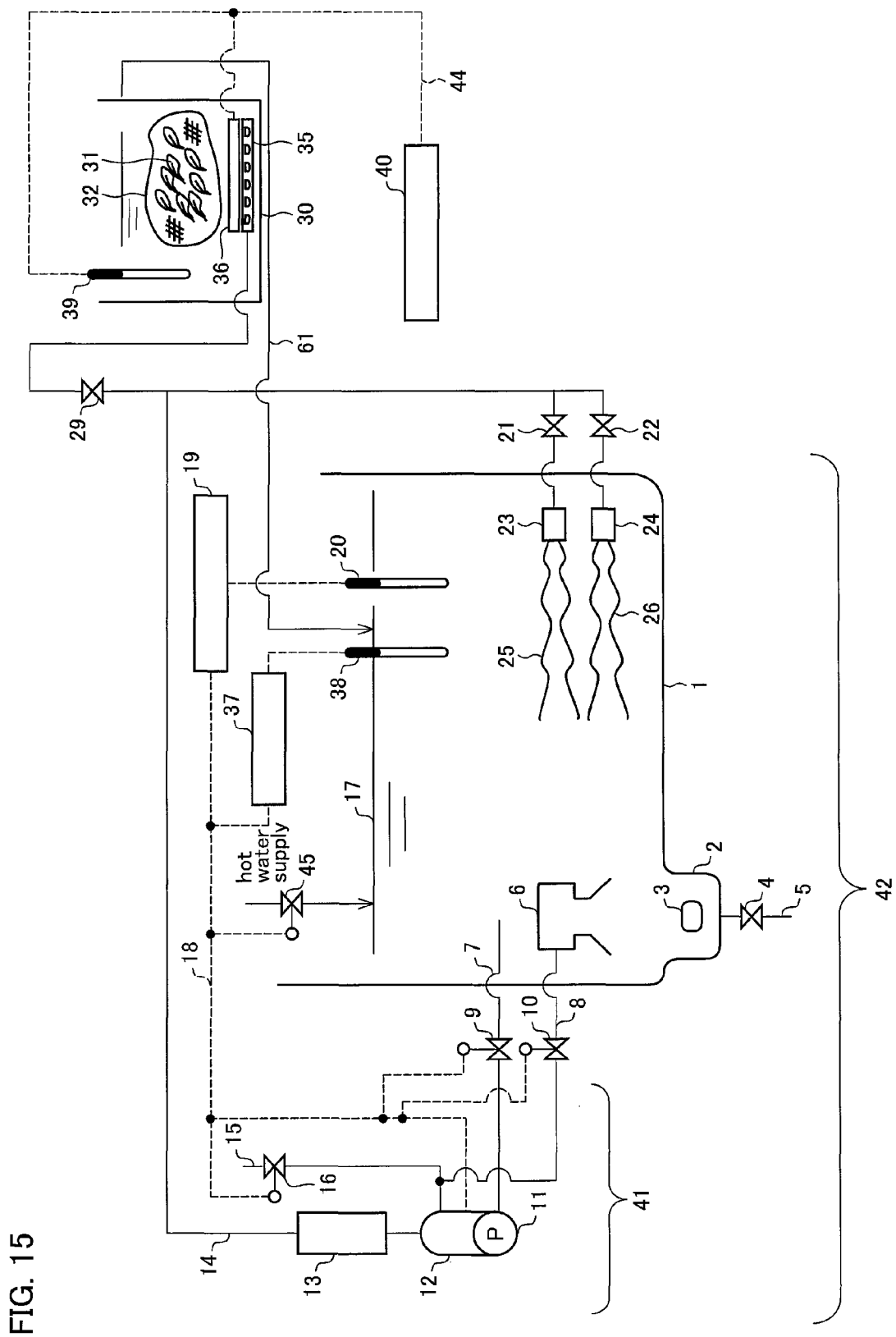
FIG. 15 is a schematic illustrating still another embodiment of a device of the present invention for increasing blood flow and an insulin-like growth factor.
Figure 16:
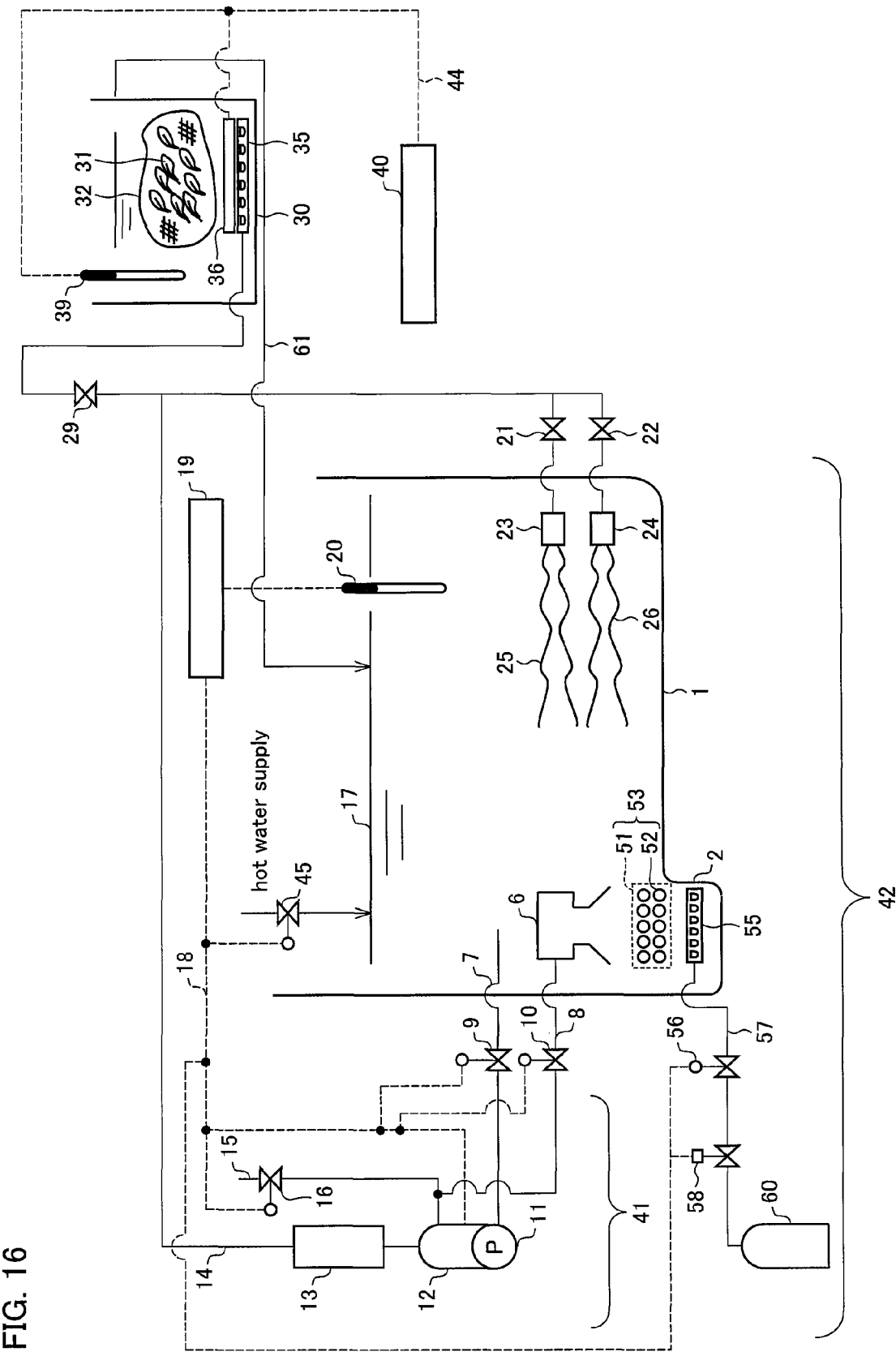
FIG. 16 is a schematic illustrating still another embodiment of a device of the present invention for increasing blood flow and an insulin-like growth factor.

As illustrated in FIGS. 15 and 16, the device of the present embodiment for increasing blood flow and an insulin-like growth factor includes the thermometer 39 in the extraction tank 30 and includes the second temperature-adjusting section 40 outside the extraction tank 30. The thermometer 39, the second temperature-adjusting section 40, and the heater 36 transmit/receive signals via a signal line 44, and as a result a temperature of bath water in the extraction tank 30 is adjusted to be a desired one. The temperature of the bath water in the extraction tank 30 is determined suitably according to the kind of the galenical 31 or the moisture-retaining agent 34.

Specifically, the thermometer 39 measures the temperature of the bath water in the extraction tank 30, and the result of the measurement is sent to the second temperature-adjusting section 40. The second temperature-adjusting section 40 stores a preset temperature of the bath water in the extraction tank 30. When the temperature of the bath water measured by the thermometer 39 is higher than the preset temperature, the second temperature-adjusting section 40 drops the temperature of the heater 36. On the other hand, when the temperature of the bath water measured by the thermometer 39 is lower than the preset temperature, the second temperature-adjusting section 40 increases the temperature of the heater 36. With the structure, the temperature of the hot water in the extraction tank 30 is adjusted according to the galenical 31 or the moisture-retaining agent 34, so that it is possible to more efficiently extract a medicinal component or a moisture-retaining component included in the galenical 31 or the moisture-retaining agent 34.

Furthermore, as illustrated in FIGS. 15 and 16, the device of the present embodiment for increasing blood flow and an insulin-like growth factor includes the thermometer 38 in the bathtub 1 and includes the first temperature-adjusting section 37 outside the bathtub 1. The thermometer 38, the first temperature-adjusting section 37, and the valve 45 transmit/receive signals via the signal line 18, and as a result the temperature of the bath water in the bathtub 1 is adjusted to be a desired one. The temperature of the bath water in the bathtub 1 may be suitably set to be a desired one. A preferable example of the temperature of the bath water in the bathtub 1 is not less than 40° C. and not more than 42° C. When the temperature of the bath water in the bathtub 1 is in this range, carbonic gas nano bubbles are particularly likely to be produced and a large amount of carbonic gas nano bubbles are absorbed via skin. This further increases blood flow and an insulin-like growth factor.

Specifically, the thermometer 38 measures the temperature of the bath water in the bathtub 1 and the result of the measurement is sent to the first temperature-adjusting section 37. The first temperature-adjusting section 37 stores a preset temperature of the bath water in the bathtub 1. When the temperature of the hot water measured by the thermometer 38 is higher than the preset temperature, the first temperature-adjusting section 37 closes the valve 45. Consequently, supply of hot water with a high temperature (e.g. hot water with a temperature higher than the preset temperature) to the bathtub 1 is stopped, which allows adjustment of the temperature of the hot water in the bathtub 1 to be the preset temperature.

On the other hand, when the temperature of the bath water measured by the thermometer 38 is lower than the preset temperature, the first temperature-adjusting section 37 opens the valve 45. Consequently, supply of hot water with a high temperature (e.g. hot water with a temperature higher than the preset temperature) to the bathtub 1 is started, which allows adjustment of the temperature of the hot water in the bathtub 1 to be the preset temperature.

Furthermore, the present invention may be arranged as follows.

It is preferable to arrange the device of the present invention for increasing blood flow and an insulin-like growth factor so that the bath water includes radium ions.

With the arrangement, the radium ions can increase the blood flow and the insulin-like growth factor, resulting in further increase in the blood flow and the insulin-like growth factor.

It is preferable to arrange the device of the present invention for increasing blood flow and an insulin-like growth factor so that the bath water includes at least one of a medicinal component and a moisture-retaining component.

With the arrangement, the bath water includes at least one of the medicinal component and the moisture-retaining component. Consequently, at least one of the medicinal component and the moisture-retaining component can be absorbed concurrently with absorption of carbonic gas nano bubbles into a body. Furthermore, since blood flow in the body increases, the medicinal component and/or the moisture-retaining component can be evenly dispersed into the body via capillaries etc., thereby increasing the effect of the medicinal component and/or the moisture-retaining component.

It is preferable to arrange the device of the present invention for increasing blood flow and an insulin-like growth factor so as to further include: carbonic gas-producing means for producing carbonic gas; and carbonic gas-retaining means for temporarily retaining the carbonic gas and thereafter supplying at least a part of the carbonic gas to the nano bubble-producing means.

With the arrangement, carbonic gas from the carbonic gas producing means is temporarily retained in the carbonic gas-retaining means, so that almost all carbonic gas can be used for preparing carbonic gas nano bubbles. Use of the carbonic gas nano bubbles allows efficiently increasing blood flow and an insulin-like growth factor.

It is preferable to arrange the device of the present invention for increasing blood flow and an insulin-like growth factor so as to further include turbulent flow forming means for discharging the carbonic gas nano bubbles into the bathtub in such a manner that the carbonic gas nano bubbles are in a turbulent flow.

With the arrangement, the carbonic gas nano bubbles in a turbulent flow are discharged into the bathtub. This enables human skin with concavities and convexes (e.g. surface of a leg) to absorb carbonic gas nano bubbles effectively. Consequently, it is possible to increase blood flow and an insulin-like growth factor.

It is preferable to arrange the device of the present invention for increasing blood flow and an insulin-like growth factor so as to further include at least one of (i) a medicinal component extraction tank for extracting a medicinal component from a galenical and (ii) a moisture-retaining component extraction tank for extracting a moisture-retaining component from a moisture-retaining agent, the carbonic gas nano bubbles being supplied into the bathtub via at least one of the medicinal component extraction tank and the moisture-retaining component extraction tank.

With the arrangement, the medicinal component is extracted in the medicinal component extraction tank and the moisture-retaining component is extracted in the moisture-retaining component. Subsequently, the carbonic gas nano bubbles containing the medicinal component and/or the moisture-retaining component are discharged into the bathtub. Consequently, the medicinal component and/or the moisture-retaining component can be absorbed via skin.

It is preferable to arrange the device of the present invention for increasing blood flow and an insulin-like growth factor so that each of the medicinal component extraction tank and the moisture component extraction tank includes a heater and a thermometer, and a temperature of the heater is adjusted according to a temperature of water in the medicinal component extraction tank or the moisture-retaining component extraction tank that is measured by the thermometer.

With the arrangement, the temperature of the water in the medicinal component extraction tank and/or the moisture-retaining component extraction tank is adjusted so as to increase efficiency in extracting a medicinal component from a galenical and/or efficiency in extracting a moisture-retaining component from a moisture-retaining agent. Consequently, it is possible to extract the effect of the medicinal component and/or the moisture-retaining component more efficiently.

It is preferable to arrange the device of the present invention for increasing blood flow and an insulin-like growth factor so that the galenical is at least one selected from the group consisting of calamus, citron, Angelica acutiloba, camomile, Cnidium officinale, dried orange peel, carrot, fennel, Scutellaria baicalensis, phellodendron bark, spruce, aloe, ginger, sweetroot, and cinnamon.

With the arrangement, pharmaceutical effects of these galenicals can be exerted in the singular or in combination on a living body.

It is preferable to arrange the device of the present invention for increasing blood flow and an insulin-like growth factor so that the moisture-retaining agent is at least one selected from the group consisting of seaweed, a fruit, liquid lanoline, glycerin, casein, olive oil, soy oil, paraffin, Vaseline, propylene glycol, and honey.

With the arrangement, moisture retention effects of these moisture-retaining agents can be exerted in the singular or in combination on a living body.

It is preferable to arrange the device of the present invention for increasing blood flow and an insulin-like growth factor so as to further include a dissolved carbonic gas meter for measuring concentration of carbonic gas dissolved in the bathtub, an amount of the carbonic gas supplied from the carbonic gas-retaining means to the nano bubble-producing means being adjusted according to a result of measurement carried out by the dissolved carbonic gas meter.

With the arrangement, the amount of carbonic gas supplied from the carbonic gas retaining means to the nano bubble-producing means is controlled so as to keep concentration of the dissolved carbonic gas in the bathtub at a desired value. That is, when the concentration of the dissolved carbonic gas in the bathtub is high, the amount of carbonic gas supplied from the carbonic gas retaining means to the nano bubble-producing means is made smaller, and when the concentration of the dissolved carbonic gas in the bathtub is low, the amount of carbonic gas supplied from the carbonic gas retaining means to the nano bubble-producing means is made larger. This enables adjustment of the concentration of the dissolved carbonic gas in the bathtub.

It is preferable to arrange the device of the present invention for increasing blood flow and an insulin-like growth factor so as to further include a bath thermometer for measuring a temperature of the bath water, an amount of hot water supplied to the bathtub being adjusted according to the temperature of the bathtub that is measured by the bath thermometer.

With the arrangement, the temperature of the bath water in the bathtub can be kept at a desired value. That is, when the temperature of the bath water in the bathtub is low, hot water with a high temperature is supplied to the bathtub, and when the temperature of the bath water in the bathtub is high, hot water with a high temperature is stopped from being supplied to the bathtub. Consequently, the temperature of the bath water can be adjusted to be a temperature suitable for skin to absorb carbonic gas nano bubbles, radium ions, a medicinal component, and a moisture-retaining component.

It is preferable to arrange the device of the present invention for increasing blood flow and an insulin-like growth factor so that the nano bubble-producing means includes: a first gas-shearing section for mixing the bath water and carbonic gas and shearing a mixture of the bath water and the carbonic gas so as to produce water containing carbonic gas micro bubbles; and a second gas-shearing section for mixing and shearing the water so as to produce water containing carbonic gas nano bubbles.

With the arrangement, only a simple structure is required to produce a large amount of carbonic gas nano bubbles.

It is preferable to arrange the device of the present invention for increasing blood flow and an insulin-like growth factor so that the first gas-shearing section includes a mixing pump for stirring the mixture of the bath water and the carbonic gas, and the mixture is stirred by the mixing pump with a rotational speed being 500 to 600 rotation/sec.

With the arrangement, the first gas-shearing section can produce a large amount of carbonic gas micro bubbles. Furthermore, with the arrangement, a rotating sheared flow that rotates at a high speed can be introduced into the second gas-shearing section, finally resulting in production of a large amount of carbonic gas nano bubbles.

It is preferable to arrange the device of the present invention for increasing blood flow and an insulin-like growth factor so that each of the first gas-shearing section and the second gas-shearing section includes a cylindrical flow path through which water containing bubbles flows, and the flow path of the first gas-shearing section is larger than the flow path of the second gas-shearing section in terms of a diameter of a circle being a cross section of the flow path.

With the arrangement, rotative speed of a rotating sheared flow introduced from the first gas-shearing section to the second gas-shearing section can be increased efficiently, and the rotating sheared flow can be made thinner efficiently. Consequently, carbonic gas micro bubbles produced in the first gas-shearing section can be sheared efficiently, resulting in production of a large amount of carbonic gas nano bubbles.

It is preferable to arrange the method of the present invention for increasing blood flow and an insulin-like growth factor so that the bath water includes radium ions.

With the arrangement, the radium ions can increase the blood flow and the insulin-like growth factor, resulting in further increase in the blood flow and the insulin-like growth factor.

It is preferable to arrange the method of the present invention for increasing blood flow and an insulin-like growth factor so that the bath water includes at least one of a medicinal component and a moisture-retaining component.

With the arrangement, the bath water includes at least one of the medicinal component and the moisture-retaining component. Consequently, at least one of the medicinal component and the moisture-retaining component can be absorbed concurrently with absorption of carbonic gas nano bubbles into a body. Furthermore, since blood flow in the body increases, the medicinal component and/or the moisture-retaining component can be evenly dispersed into the body via capillaries etc., thereby increasing the effect of the medicinal component and/or the moisture-retaining component.

It is preferable to arrange the method of the present invention for increasing blood flow and an insulin-like growth factor so that the medicinal component is derived from a galenical that is at least one selected from the group consisting of calamus, citron, Angelica acutiloba, camomile, Cnidium officimale, dried orange peel, carrot, fennel, Scutellaria baicalensis, phellodendron bark, spruce, aloe, ginger, sweetroot, and cinnamon.

With the arrangement, pharmaceutical effects of these galenicals can be exerted in the singular or in combination on a living body.

It is preferable to arrange the method of the present invention for increasing blood flow and an insulin-like growth factor so that the moisture-retaining component is derived from a moisture-retaining component that is at least one selected from the group consisting of seaweed, a fruit, liquid lanoline, glycerin, casein, olive oil, soy oil, paraffin, Vaseline, propylene glycol, and honey.

With the arrangement, moisture retention effects of these moisture-retaining agents can be exerted in the singular or in combination on a living body.

As described above, in the device and the method of the present invention for increasing blood flow and an insulin-like growth factor, bath water including carbonic gas nano bubbles is caused to touch skin, so that carbonic gas nano bubbles is absorbed into a body via skin.

Therefore, it is possible to increase the amount of carbonic gas only a little amount of which has been conventionally absorbed via the surface of skin. Furthermore, the carbonic gas absorbed via skin is taken into capillaries, and thus circulates through and diffuses into a whole body. Consequently, it is possible to increase blood flow and the amount of an insulin-like growth factor.

It is known that the insulin-like growth factor is related to various diseases (such as central nerve diseases, cardiovascular system diseases, metabolic disorder diseases, digestive organ diseases, locomotory diseases, and dermatological diseases). To be more specific, examples of the central nerve diseases include Alzheimer and dementia. Examples of the cardiovascular system diseases include chronic cardiac failure, high blood pressure, cerebral infarction, and cardiac infarction. Examples of the metabolic disorder diseases include diabetes, obesity, and hyperlipemia (i.e. metabolic syndrome). Examples of the digestive organ diseases include gastric ulcer and liver disease. Examples of the locomotory diseases include rheumatoid arthritis and arthritis. Examples of the dermatological diseases include aging of skin and alopecia. Furthermore, it is known that the insulin-like growth factor contributes to the improvement of various diseases through promotion of growth of red blood cells or activation of immune function (e.g. activation of natural killer cells). Therefore, the device and the method of the present invention for improving blood flow and an insulin-like growth factor allows increases in blood flow and the insulin-like growth factor, resulting in treatments of the diseases.

In addition, the carbonic gas nano bubbles are highly effective in cleaning skin of a human body, resulting in reduction of facial wash, shampoo, and body soap.

As described above, in the present invention, bath water that includes carbonic gas nano bubbles and that is accumulated in the bathtub touches skin, so that it is possible to increase blood flow and an insulin-like growth factor. Therefore, the present invention is applicable to treatments of various diseases (such as central nerve diseases, cardiovascular system diseases, metabolic disorder diseases, digestive organ diseases, locomotory diseases, and dermatological diseases), and to fields relating to the treatments of the diseases.

EXAMPLES

Example 1

It was confirmed that carbonic gas nano bubbles were produced by the device of the present invention for increasing blood flow and an insulin-like growth factor.

The bathtub 1 was a bathtub of 200 liters in capacity, and the gas-liquid mixture-circulating pump 11 was a pump having a three-phase motor 200V×3.7 KW. The amount of air from the pipe 15 was set to 0.7 liter/min. The carbonic gas-bubbling solid agent 3 was "Bub®" manufactured by Kao Corporation.

The diameter of the cross section of the cylindrical flow path of the micro bubble-producing section 12 was set so that the diameter of an opening to discharge micro bubble white-clouded water was 50 to 80% of the diameter of an opening to absorb a gas-liquid mixture (absorbing opening of the gas-liquid mixture-circulating pump 11). Specifically, the diameter of the discharge opening was set to 8 mm.

Furthermore, the shape of the cross section of the cylindrical flow path of the gas-shearing section 13 was set to be 80% or less-downsized shape of the cross section of the cylindrical flow path of the micro bubble-producing section 12. Specifically, the diameter of the discharge opening was set to 6 mm.

Furthermore, the inside of the cylindrical flow path of the gas-shearing section 13 (second gas-shearing section) was polished in order to reduce frictional resistance. Furthermore, the flow path was provided with two or more grooves each of 0.3 to 0.6 mm in depth and 0.8 mm or less in width in order to prevent generation of a rotating turbulent flow. Furthermore, a material that formed the flow path of the gas-shearing section 13 had a thickness of 6 to 12 mm in order to prevent a decrease in energy of movement of a fluid that was caused by vibration of the material.

On the other hand, in a control experiment for the device of the present invention for increasing blood flow and an insulin-like growth factor, the bathtub 1 was a bathtub of 200 liters in capacity and the gas-liquid mixture-circulating pump 11 was a pump having a single-phase motor 100V×0.4 KW. The amount of air from the pipe 15 was set to 1 liter/min. The carbonic gas-bubbling solid agent was not used.

The diameter of bubbles produced by the device was measured by an LS particle size distribution analyzer (manufactured by Beckman Coulter, Inc.). A specific method for the measurement was according to the protocol attached to the LS particle size distribution analyzer.

Figure 17:
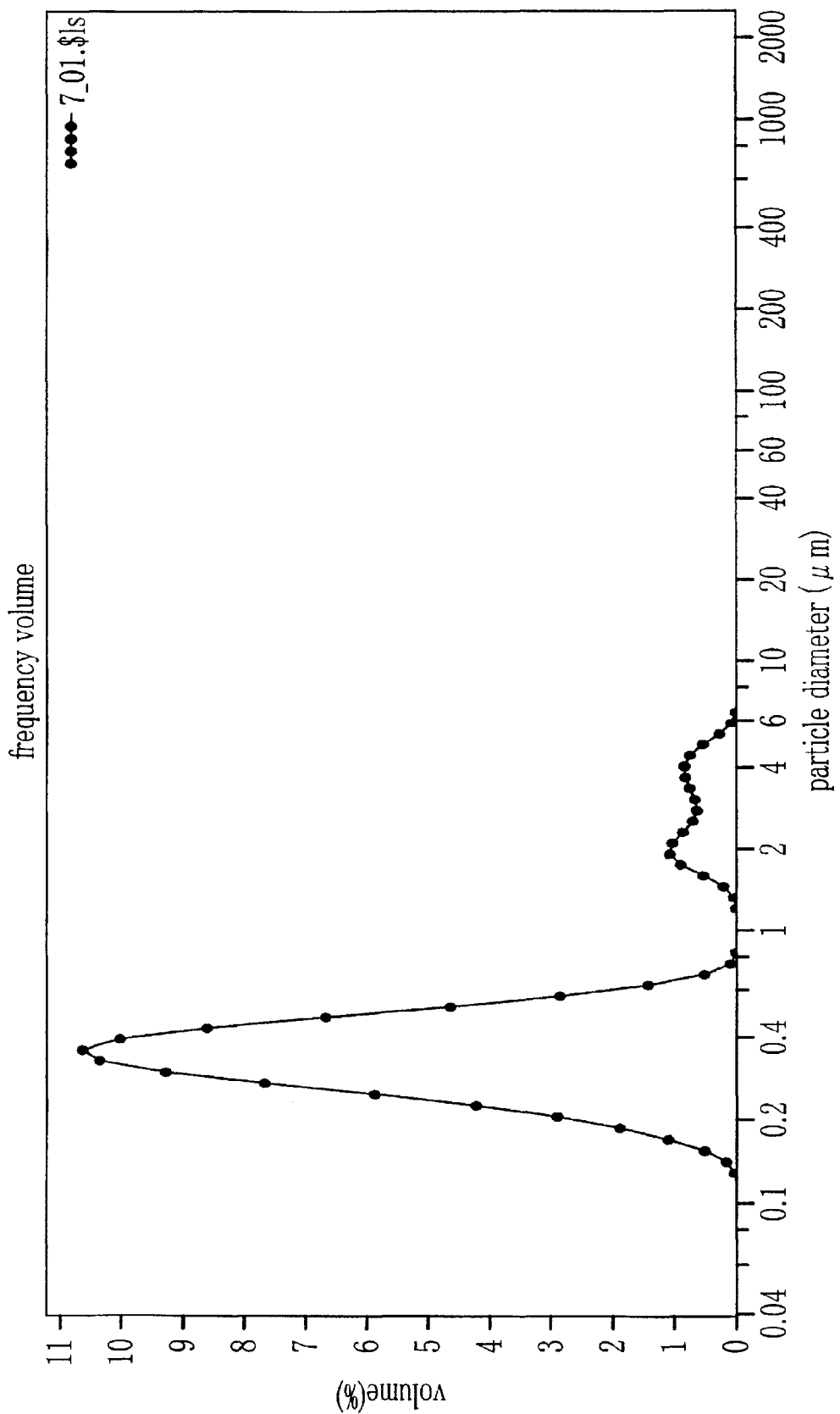
FIGS. 17(a) to 17(c) are graphs each showing a diameter of a carbonic gas bubble produced by the device of the present invention for increasing blood flow and an insulin-like growth factor.

As illustrated in FIGS. 17(a) and 17(b), the measurement showed that a large part (volume (%) was 10.6) of carbonic gas nano bubbles produced by the device of the present invention for increasing blood flow and an insulin-like growth factor were bubbles of 0.342 μm (342 nm) in diameter. As illustrated in FIG. 17(c), an average size of the carbonic gas nano bubbles produced by the device of the present invention for increasing blood flow and an insulin-like growth factor was 0.629 μm (629 nm).

Figure 18:
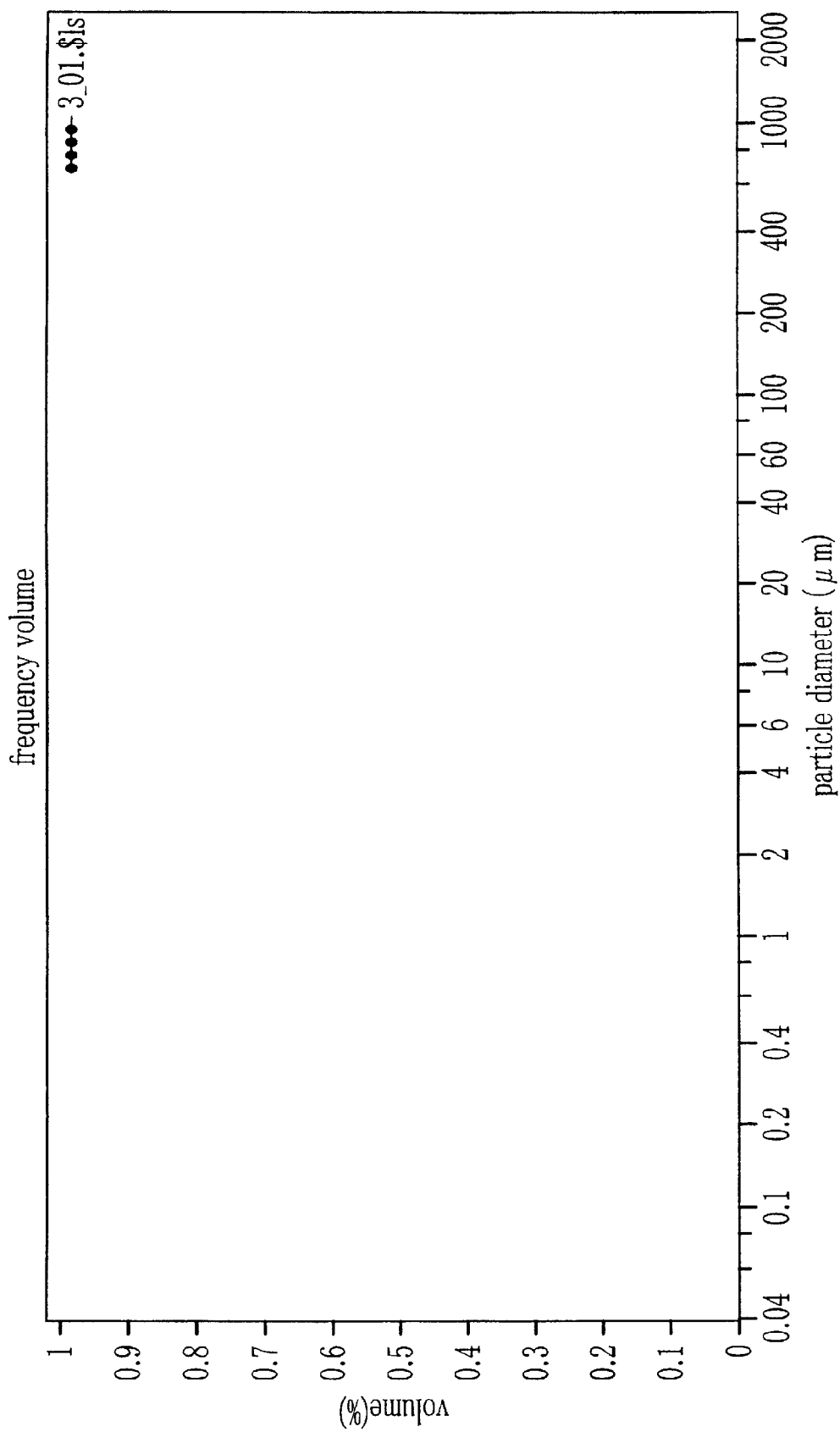
FIGS. 18(a) to 18(c) are graphs each showing a diameter of a carbonic gas bubble produced by a conventional technique.

On the other hand, as illustrated in FIGS. 18(a), (b), and (c), carbonic gas nano bubbles were not observed in the control experiment.

Example 2

Using the device of the present invention for increasing blood flow and an insulin-like growth factor of Example 1, a treatment in which carbonic gas nano bubbles were jetted to legs (of a 57 year-old human) for approximately 20 min/day was made. The treatment was made for 60 days.

After the treatment, the amount of secreted insulin and blood sugar level of the human were measured. As the insulin-like growth factor increases, more amount of insulin is secreted from a pancreas. Therefore, an increase/decrease in the amount of the insulin-like growth factor can be determined by measuring the amount of insulin.

The amount of secreted insulin and blood sugar level were measured through a glucose tolerance test. Specifically, the amount of secreted insulin and blood sugar level were measured after 0 minute, 30 minutes, 60 minutes, 120 minutes, and 180 minutes from the time when the human had drunken 75g of a glucose solution. The measurement was made in the Japanese Red Cross Hospital through a known method. A control experiment was made before the treatment in the same way. Tables 1 and 2 show the results of the experiments.

TABLE 1

|  | 0 min later | 30 min later | 60 min later | 120 min later | 180 min later |
|---|---|---|---|---|---|
| Blood sugar level (mg/dl) | 132 | 212 | 289 | 348 | 299 |
| Amount of insulin (μU/ml) | 1.4 | 4.0 | 6.5 | 8.5 | 5.7 |

TABLE 2

|  | 0 min later | 30 min later | 60 min later | 120 min later | 180 min later |
|---|---|---|---|---|---|
| Blood sugar level (mg/dl) | 102 | 173 | 239 | 266 | 146 |
| Amount of insulin (μU/ml) | 3.1 | 7.0 | 9.8 | 13.1 | 10.8 |

Table 1 shows the result of the measurement before the treatment with carbonic gas nano bubbles. Table 2 shows the result of the measurement after the treatment with carbonic gas nano bubbles. The results of the measurements showed that the treatment with the carbonic gas nano bubbles increased the amount of insulin and dropped the blood sugar level. In addition, the results showed that the treatment with the carbonic gas nano bubbles increased the insulin-like growth factor.

Example 3

Using the device of the present invention for increasing blood flow and an insulin-like growth factor of Example 1, a treatment in which carbonic gas nano bubbles were jetted to legs of test subjects for approximately 20 min/day was made. The treatment was made on three test subjects for 60 days ("number" in Tables 3 and 4 indicates individual test subjects).

Table 3 shows the results of measurements of blood sugar level, blood pressure, the amount of meal, and body weight before the treatment with carbonic gas nano bubbles. Table 4 shows the results of measurements of blood sugar level, blood pressure, the amount of meal, and body weight after the treatment with carbonic gas nano bubbles. Specifically, as shown in Table 3, the average value of fasting blood sugar level before the treatment was 160 mg/dl, and the average value of after-supper blood sugar level before the treatment was 231 mg/dl. On the other hand, as shown in Table 4, the average value of fasting blood sugar level after the treatment was 141 mg/dl, and the average value of after-supper blood sugar level after the treatment was 127 mg/dl. The results of the measurements showed that the treatment with carbonic gas nano bubbles dropped the blood sugar level.

TABLE 3

| Number | Fasting blood sugar level (mg/dl) | After-lunch blood sugar level (mg/dl) | After-supper blood sugar level (mg/dl) | Fasting blood pressure (mmHg) | After-lunch blood pressure (mmHg) | After-supper blood pressure (mmHg) | Amount of meal (calorie) | Weight (kg) |
|---|---|---|---|---|---|---|---|---|
| 1 | 150 | 164 | 253 | 139 | 88 | 86 | 2000 | 60.2 |
| 2 | 152 | 128 | 258 | 111 | 72 | 83 | 2000 | 60.6 |
| 3 | 179 | 176 | 183 | 92 | 86 | 65 | 2000 | 59.3 |

TABLE 4

| Number | Fasting blood sugar level (mg/dl) | After-lunch blood sugar level (mg/dl) | After-supper blood sugar level (mg/dl) | Fasting blood pressure (mmHg) | After-lunch blood pressure (mmHg) | After-supper blood pressure (mmHg) | Amount of meal (calorie) | Weight (kg) |
|---|---|---|---|---|---|---|---|---|
| 1 | 146 | 122 | 130 | 120 | 88 | 82 | 2000 | 59.5 |
| 2 | 152 | 118 | 168 | 116 | 85 | 79 | 2000 | 58.8 |
| 3 | 124 | 101 | 84 | 117 | 84 | 76 | 2000 | 59.5 |

Example 4

Hemoglobin A1c (glycosylated hemoglobin), i.e. HbA1c (%) is data indicative of the condition of a diabetic patient. HbA1c (%) is data indicative of a long-term change of the condition of the diabetic patient. Since hemoglobin in a blood is metabolized in one or two months, HbA1c (%) is considered as being indicative of the average value of blood sugar level in one or two months. The degree of progression of diabetes is determined according to HbA1c (%).

Therefore, it was examined to what degree HbA1c (%) was changed by making the treatment with carbonic gas nano bubbles with use of the device of the present invention for increasing blood flow and an insulin-like growth factor of Example 1. Specifically, HbA1c (%) was measured before the treatment with carbonic gas nano bubbles and after 7 months from the time the treatment started. HbA1c (%) was measured in the Japanese Red Cross Hospital through a well known method. The change of HbA1c (%) of a 57 year-old human was examined.

Before the treatment with carbonic gas nano bubbles, HbA1c (%) was 9.4(%). On the other hand, after 7 months from the time the treatment started, HbA1c (%) was 5.4(%). A normal value of HbA1c (%) ranges from 4.3 to 5.8(%). HbA1c (%) of a person with mild diabetes ranges from 5.8 to 6.5(%).

Example 5

A treatment in which carbonic gas nano bubbles were jetted to legs for approximately 20 minutes was made. Thereafter, volume of blood flowing in a blood vessel positioned 1 to 2 mm internally away from the surface of skin was measured several times. The measurement of blood flow was made with a blood flowmeter (manufactured by OMEGA-WAVE, INC.). A specific method for the measurement was according to the protocol attached to the blood flow meter.

Blood flow (unit: Q/Q0) after the treatment with carbonic gas nano bubbles was 1.3 to 1.6 times larger than that before the treatment with carbonic gas nano bubbles.

Example 6

Using the device of the present invention for increasing blood flow and an insulin-like growth factor, a treatment to jet carbonic gas nano bubbles to legs was performed. Table 5 shows changes of blood flow at that time. In Table 5, Q/Q0 indicates a value obtained by dividing blood flow without the treatment by blood flow after the treatment was performed for a predetermined time. Measurement of blood flow was carried out through a publicly known method.

TABLE 5

| | Without treatment 0 min later | With treatment 5 min later | With treatment 10 min later | With treatment 15 min later | With treatment 20 min later | With treatment 25 min later |
|---|---|---|---|---|---|---|
| Q/Q0 | 1 | 1.2 | 1.3 | 1.4 | 1.6 | 1.6 |

As shown in Table 5, when the treatment was performed for 25 minutes, blood flow increased 1.6 times.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

What is claimed is:

1. A device for increasing blood flow and an insulin-like growth factor, comprising:
    a bathtub; and
    nano bubble-producing means for producing carbonic gas nano bubbles in bath water in the bathtub;
    the nano bubble-producing means includes:
    a first gas-shearing section for mixing the bath water and carbonic gas and shearing a mixture of the bath water and the carbonic gas so as to produce water containing carbonic gas micro bubbles; and
    a second gas-shearing section for mixing and shearing the water so as to produce water containing carbonic gas nano bubbles; wherein
    each of the first gas-shearing section and the second gas-shearing section includes a cylindrical flow path through which water containing bubbles flows, and
    the flow path of the first gas-shearing section is larger than the flow path of the second gas-shearing section in terms of a diameter of a circle being a cross section of the flow path.

2. The device as set forth in claim 1, wherein the bath water includes radium ions.

3. The device as set forth in claim 1, wherein the bath water includes at least one of a medicinal component and a moisture-retaining component.

4. The device as set forth in claim 1, further comprising:
    carbonic gas-producing means for producing carbonic gas; and
    carbonic gas-retaining means for temporarily retaining the carbonic gas and thereafter supplying at least a part of the carbonic gas to the nano bubble-producing means.

5. The device as set forth in claim 1, further comprising turbulent flow forming means for discharging the carbonic gas nano bubbles into the bathtub in such a manner that the carbonic gas nano bubbles are in a turbulent flow.

6. The device as set forth in claim 1, further comprising at least one of (i) a medicinal component extraction tank for extracting a medicinal component from a galenical and (ii) a moisture-retaining component extraction tank for extracting a moisture-retaining component from a moisture-retaining agent,
    the carbonic gas nano bubbles being supplied into the bathtub via at least one of the medicinal component extraction tank and the moisture-retaining component extraction tank.

7. The device as set forth in claim 6, wherein
    the medicinal component extraction tank and/or the moisture component extraction tank includes a heater and a thermometer, and
    a temperature of the heater is adjusted according to a temperature of water in the medicinal component extraction tank or the moisture-retaining component extraction tank that is measured by the thermometer.

8. The device as set forth in claim 6, wherein the galenical is at least one selected from the group consisting of calamus, citron, *Angelica acutiloba*, camomile, *Cnidium officinale*, dried orange peel, carrot, fennel, *Scutellaria baicalensis*, phellodendron bark, spruce, aloe, ginger, sweetroot, and cinnamon.

9. The device as set forth in claim 6, wherein the moisture-retaining agent is at least one selected from the group consisting of seaweed, a fruit, liquid lanoline, glycerin, casein, olive oil, soy oil, paraffin, Vaseline, propylene glycol, and honey.

10. The device as set forth in claim 4, further comprising a dissolved carbonic gas meter for measuring concentration of carbonic gas dissolved in the bathtub,
   an amount of the carbonic gas supplied from the carbonic gas-retaining means to the nano bubble-producing means being adjusted according to a result of measurement carried out by the dissolved carbonic gas meter.

11. The device as set forth in claim 1, further comprising a bath thermometer for measuring a temperature of the bath water,
   an amount of hot water supplied to the bathtub being adjusted according to the temperature of the bathtub that is measured by the bath thermometer.

12. The device as set forth in claim 1, wherein
   the first gas-shearing section includes a mixing pump for stirring the mixture of the bath water and the carbonic gas, and
   the mixture is stirred by the mixing pump with a rotational speed being 500 to 600 rotation/sec.

* * * * *